(12) United States Patent
Metcalf et al.

(10) Patent No.: US 6,238,275 B1
(45) Date of Patent: May 29, 2001

(54) CONTAINED DIRECT PARTICLE BEAM FLOW ABRASION SYSTEM

(76) Inventors: Alva Wesley Metcalf, 28 Belcrest, Laguna Niguel, CA (US) 92677; Calvin Lon Carrier, 33 Seabrook Dr., Dana Point, CA (US) 92629

( * ) Notice: Subject to any disclaimer, the term of this patent is extended or adjusted under 35 U.S.C. 154(b) by 0 days.

(21) Appl. No.: 09/136,862

(22) Filed: Aug. 19, 1998

(51) Int. Cl.[7] .................................................. B24B 1/00
(52) U.S. Cl. .......................... 451/87; 451/88; 451/99; 451/101; 451/102; 451/446
(58) Field of Search .................. 451/87, 88, 99, 451/101, 102, 446

(56) References Cited

U.S. PATENT DOCUMENTS

| | | |
|---|---|---|
| 3,815,286 | 6/1974 | Piet . |
| 5,037,432 | * 8/1991 | Molinari ................................ 606/131 |
| 5,207,234 | * 5/1993 | Rosso .................................. 128/898 |
| 5,971,999 | * 10/1999 | Naldoni ............................... 606/131 |

FOREIGN PATENT DOCUMENTS

| | | |
|---|---|---|
| 2140191 | 2/1972 | (DE) . |
| 0 258 901 | * 9/1988 | (EP) ............................. A61B/17/32 |
| 0324448 | 7/1989 | (EP) . |
| 0564392 A2 | * 3/1993 | (EP) ............................. A61B/17/54 |
| 0564392A2 | 10/1993 | (ES) . |
| 2164126 | 3/1986 | (GB) . |
| 9711650 | 4/1997 | (GB) . |
| 0806184A1 | 11/1997 | (IT) . |
| 0258901 | 3/1988 | (JP) . |
| 8505041 | 11/1985 | (WO) . |
| WO 99/23951 | * 3/1993 | (WO) ............................. A61B/17/00 |
| WO 97/11650 | * 4/1997 | (WO) ............................. A61B/17/54 |

* cited by examiner

Primary Examiner—Joseph J. Hail, III
Assistant Examiner—Shantese McDonald
(74) Attorney, Agent, or Firm—Stetina, Brunda, Garred & Brucker

(57) ABSTRACT

Systems for abrasive action include machinery for creating a vacuum and positive pressure to enable flow control while providing adequate vacuum to both retrieve and capture the spent abrasive material and the abraded material. A first embodiment includes a vacuum and boost operation facilitated by the use of a foot control for high control of abrasion, cleaning and polishing. A second embodiment is for use with human tissue and includes a vacuum only system with filtered air. A third embodiment includes vacuum with automatic boost for skilled medical personnel use and uses a minimum vacuum level to trigger a pre-set boost operation. The system utilizes air filtration, ultra violet, heat oven sterilization and secure waste storage. A manual contact tool is used closely with the area to be abraded supplanting any other control other than the pressing of the manual contact tool against the surface to be abraded, to create sufficient vacuum to trigger boost operation. A hand-held direct particle beam abrasion manual contact tool having a prophylactic tip which creates a concentric space within which the kinetics of focussed direct impact and radial collection of spent abrasive particles and abraded material is collectably withdrawn. A flow accelerator within an annular insert of the manual contact tool and prophylactic tip can be varied to suit many applications.

43 Claims, 12 Drawing Sheets

CONTAINED DIRECT PARTICLE BEAM FLOW ABRASION SYSTEM

FIELD OF THE INVENTION

The present invention relates to the field of controlled directed abrasion by impact of abrasive particles, and a system for providing advantageous control of the geometry of impact and collection, as well as the process flow conditions, safety and sanitation of the spent abrasive particles and abraded material.

BACKGROUND OF THE INVENTION

The use of particles to abrade contacted surface areas is well known. Particles can moved by kinetic energy to remove material from other surfaces, as by buffing, polishing, tumbling and by directed flow of particles in a carrier media. The best known large scale example of directed flow of particles in a carrier media is sand blasting. Sand blasting is done using industrial scale equipment, consuming bags of generally screened, but non-uniform size particles. A high air pressure is used to spray the sand on the surface to be impacted, thereby causing abrasion of the surface and with higher pressure cause actual cutting of the material For smaller sized applications, the sand size is more tightly uniform. For indoor use, and for reasons of cleanliness and sanitation, the collection of spent sand must also be accommodated. In U.S. Pat. No. 5,037,432, a hand held device which facilitates the collection of spent sand is illustrated. In this device it is stated as an essential element, that the flow of sand impinge upon the surface to be abraded at an inclined angle. In fact, the device of this patent is designed primarily toward the circularity of the return path of the spent sand, and provides an opening for abrasion as part of the circular path of travel of the abrading material. Abrasion is caused by having the abrading material pass laterally by the surface of material to be abraded and by a sloughing action removes material. The material is removed in a non-linear fashion with most material removed at the upstream end of exposure of the surface to be abraded in the path of circular flow of the abrading material. The abrasion of the material surface downstream of the initial contact is caused by tumbling of the media and further mixed sloughing. Because of the shallow angle of attack, at least half or more of the kinetic energy in the particles is used to move them along in a tumbling fashion end over end, meaning that less than half of the kinetic energy of the particles can be applied to abrade the target surface. These design characteristics makes the tool inefficient and limits its use for various applications. Further, such inefficient use translates into the wasting use of abrading material. Three to five times as much abrading material will be used to remove a given amount of material to be removed as would otherwise be necessary.

Control of the flow of the abrasion material is critical for small scale applications and especially where delicate work is to be performed. As such the control system should be able to produce a smooth and even control of abrasive force to be applied. The tool should facilitate accurate control by allowing an even and proportional application of force. Removal of abraded material should occur through impact, and not inefficient lateral sloughing and trough digging.

Further, because the stream of flowing particles abrades the surface at an angle, a sharp focus cannot be achieved. Etch writing or other closely tolleranced work cannot be performed both due to the spreading of the stream of abrasive media, as well as due to uneven application of energy to the abraded surface.

Another problem with conventional abrasion devices is the creation of pollution in that the abraded material is not always safely collected and isolated. For example, industrial paint stripping operations with lead based paint in which the removed material is allowed to settle like ordinary dirt can provide ground contamination both around the plant and at the land fill. In addition, where the abrasive material and removed material are not collected for safe disposal, workers are exposed to airborne contaminants.

Filtering the abraded waste material along with the particulates of the abrasive material presents an especial problem. In most cases the size of the abraded waste material will vary in size from flakes larger than the abrasive material, to a fine powder much smaller than the abrasive material. Collection must be had with extreme filtration of the most fine particles, but also without having to provide an expanded surface filter which must be changed continually over a series of short periods of time. Collection of the spent abrasive material may also result in its being treated to remove the abraded material and then recycled, if such is economically feasible.

Control and isolation of abraded material is even more of an issue in medical applications where the abrasive material is used to remove skin in medical procedures involving active acne, acne scars, blackheads, tattoos, or other skin conditions such as psoriasis and exema. Skin removal must be done gently to avoid cutting the skin and abrading past the point where blood vessels are encountered. Skin as abraded material should be isolated and prevented from re-use without having formal sterilization and re-processing. All abraded skin should be treated as contaminated medical waste and should be collected into a waste collection space which includes a sealed container with back flow protection and ultimately formal destruction and proper disposal.

SUMMARY OF THE INVENTION

The system of this invention includes machinery for both creating a vacuum and positive pressure to enable a wide range of control while providing adequate vacuum throughout the range to both retrieve and capture the spent abrasive material and the abraded material. A first embodiment of the system includes a vacuum and boost operation facilitated by the use of a foot control and which is especially useful for high control of abrasion, cleaning and polishing of various surfaces. A second embodiment is for use with human tissue, especially by cosmetological personnel and would include a vacuum only system. A third embodiment includes vacuum and air boost operation and is intended for skilled medical personnel and uses a pre-set minimum vacuum level to enable the boost operation and which allows an operator to use a surface abrading tool which may preferably be a manual contact tool which works closely in contact with the area to be abraded without the need to independently operate a foot pedal control or any other control other than the pressing of the manual contact tool against the surface to be abraded. All embodiments feature a hand-held "direct particle beam abrasion manual contact tool" having a prophylactic tip which creates a concentric space within which the kinetics of focussed impact and collection of the spent abrasive particles and abraded material mix is collectably withdrawn. In terms of geometry within the replaceable plastic cap tip, the tool provides a highly focused and focusable stream of abrasion material and also provides for a concentrically distributed series of removal ports so that the spent abrasive material will be immediately removed from the abrasive material impact area, allowing the full energy of each abrasive particle full contact with the surface to be abraded. The prophylactic tip is inexpensive and replaceable, preferably made of ordinary plastic, and therefore very advantageous where used with any material surface. The prophylactic tip is available with several different sized openings to more finely define the surface area in which the abrasive material may be directed.

The manual contact tool comes with a flow accelerator as an annular insert which can be changed. The annular insert can have a longer tip for a more focussed stream of accelerated abrasive impact, or a shorter tip for a wider stream of accelerated abrasive impact. A variety of annular inserts having various internal bore sizes in combination with various tip lengths may be advantageously used with a combination of shapes and sizes of plastic caps to adjust the velocity and flow area of the stream of abrasive material.

The prophylactic tip in combination with the even radial distribution of return channels in the hand held tool creates a somewhat toroidal pattern which serves two purposes. First, in combination with the aforementioned "flow accelerator insert" the tip and its design (based upon application) will provide a radial vacuum to the abrasive beam and splay the beam to a predetermined shape prior to impact with the material to be abraded. The second purpose is for even retrieval of spent abrasive and abraded material in a stream that is equally radially pulled in all directions (360°) from dead center of the tip. The full energy in each of the abrasive particles is spent onto the surface to be abraded and the inter particle collisions are minimized or eliminated by design.

The system uses both vacuum and a pressurized boost with independent controls so that an operator can quickly control the on and off function, as well has pressure boost(in one configuration operable with an instant response foot control), so that the operator can focus concentration on the area of the object being abraded.

A supply canister has a pickup tube having a tiny hole which draws the abrasive material by venturi action into a supply line. The supply canister can operate while the abrasion material supply system is in vacuum only mode or in full pressurized mode. A vacuum bleed valve is used to provide a supply of air carrier to a supply canister while in vacuum mode and which is used as a dampener when the system transitions to pressurized operation. An air inlet adjustment valve controls the amount of shunt air into the material supply canister. When the air inlet supply is off, the air into the supply canister is at minimum and occurring only through the vacuum bleed valve. When the air inlet supply is on, additional air is supplied to the supply canister, and additional flow of abrasive particles results. Under pressurized control, an open condition shunts or diverts air away from the supply canister to buffer and weaken the pressure supplied to the supply canister to shorten the control range.

A second valve is used to shunt air into the vacuum line near the end of the vacuum path to likewise control the magnitude of operation under vacuum operation, and which can dampen or limit the air to the supply canister while under air boost operation. This valve is expected to be fully closed under pressure boost operation so that enough vacuum will be present to move abrasion particles and abraded material along the exit line as the pressure causes a higher rate of flow of the particles at the target. A customized three way solenoid valve and vacuum sensor is used to monitor vacuum and will not allow boost operation when the pressure in the tip of the manual contact tool is below a pre-set vacuum level, which will allow the introduction of abrasive media only during conditions when adequate used media scavenging or collection can occur.

A specialized set of hollow core fed valves used as the first and second control valves will facilitate an ability of the operator to more easily and linearly control the flow of particles and vacuum. The active core of the valve presents a moving series of sets of apertures to the flow channel as the valve is turned. The total cross sectional area available for flow changes so gradually with regard to the angular displacement of the core, that a smooth, proportional control is achieved, preferably through a 180° rotation of either valve.

BRIEF DESCRIPTION OF THE DRAWINGS

The invention, its configuration, construction, and operation will be best further described in the following detailed description, taken in conjunction with the accompanying drawings in which.

DETAILED DESCRIPTION OF THE PREFERRED EMBODIMENT

The description and operation of the contained direct particle beam flow abrasion system of the present invention will be best described with reference to FIG. 1. It is believed that the invention will be best explained with respect to a concrete configuration and then with respect to a schematic representation embodied in the configuration shown, and then by variations in aspects of the invention.

Figure 1:
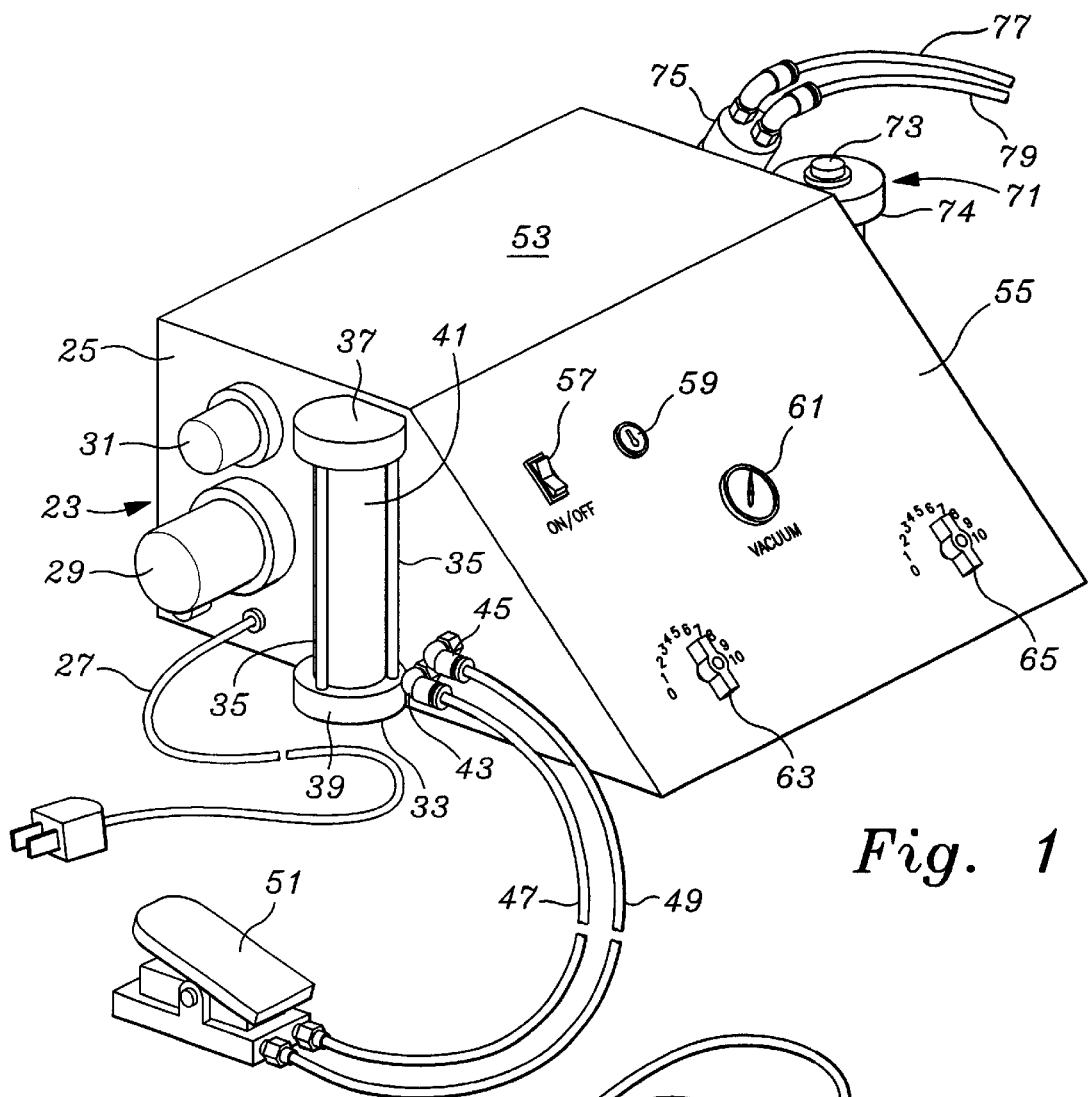
FIG. 1 is a perspective left side view of a housing for one size of the system of the present invention, about the size of a suitcase, and showing several external features thereof, including the filters, waste canister and pedal operated power boost.

FIG. 1 is a perspective view of an abraision device with supply and collection, referred to as system 21. System 21 resides within a housing 23 which may be made of a single trifold length of metal including a base (not seen) and upward folded sides, one of which is seen as side 25. An electric power cord 27 is seen, as is a separator and separator system shown as a primary filter 29 and a secondary filter 31. It is understood that there are a myriad of ways in which spent abraisive material and abraded material may be removed from a flowing air stream, including both wet and dry methods, filtering, cyclones, liquid adsorption and the like. Filters are utilized and explained because they are believed to offer the best advantages in a compact, portable system.

A waste collection space is provided in the form of a waste cannister 33 which is seen attached to and extending from the side 25. The waste collection space may be otherwise provided either within or remote from housing 23 or any housing described with regard to this invention. Waste cannister is connected to other components in the system 21 through the wall 25 from which it is supported. A series of vertical connecting rods 35 may be used to hold the waste cannister 33 together and join a top plate 37 and a bottom plate 39 to a cylindrical portion 41 which may be made of glass or other transparent material to give a visual indication of the fullness of the waste cannister 33.

Seen in FIG. 1 are a pair of quick connect fittings 43 and 45 to which are connected hoses 47 and 49 respectively. Quick connect fittings 43 and 45 have release rings which facilitate the insertion and locking of the ends of tubing, which preferably be about 0.375 inch in diameter tubing, and hold it in place. This type of quick release fitting enables quick disengagement of the hoses 47 and 49 by simultaneously pulling the hose while pushing the retaining ring back and into the fitting.

A foot pedal control 51 has a quick open valve and actuation of the control 51 puts the hoses 47 and 49 into communication to make a stream of pressurized air available to the abraisive material supply. Atop the housing 23 is a cover plate 53. Cover plate 53 abuts a front plate 55 which supports most of the controls of the system 21.

Front plate 55 supports an ON/OFF rocker switch 57 which is used to turn the system 21 on and off, but only providing the lockout key is inserted into the lockout safety switch 59 and that the lockout safety switch 59 is closed. At the center of the front plate 55 is a gauge 61 to indicate the amount of vacuum in the system, typically measured from a point downstream of the secondary filter 31. In addition, guage 61 may also indicate positive pressure in the stream of pressurized air going to the supply of abraisive material, or such a guage may be located elsewhere on the front plate 55.

To one side of the guage 61 a valve handle 63 is surrounded by a series of numerical designations on the front plate 55 which give a visual indication of the displacement of the valve handle 63. Location is a matter of choice, but this position is typically occupied by the vacuum bleed valve control. To one side of the handle 63 is another similarly located handle 65 which typically controls the inlet shunt for the abraisive material supply feed air, and is referred to as a shunt since it parallels a pressure sensitive check valve typically located inside the housing 23.

Partially seen in FIG. 1 is a supply cannister assembly 71 with a top plate 74, fill cap 73 and a manual contact tool 75. It is understood that any surface abrading tool can be used in any of the systems disclosed herein, but that since many of the component parts of the systems disclosed work well with an enclosure placed over the surface to be abraded, and for fullness of disclosure the manual contact tool 75 will be used to demonstrate all of the advantages of the invention. Other surface abrading tools are well known and may be employed with the systems of the invention disclosed herein to result in varying degrees of advantage. A pair of hoses 77 and 79 extend to connect to the tool 75 and are abraisive material supply and return hoses, respectively.

Figure 2:
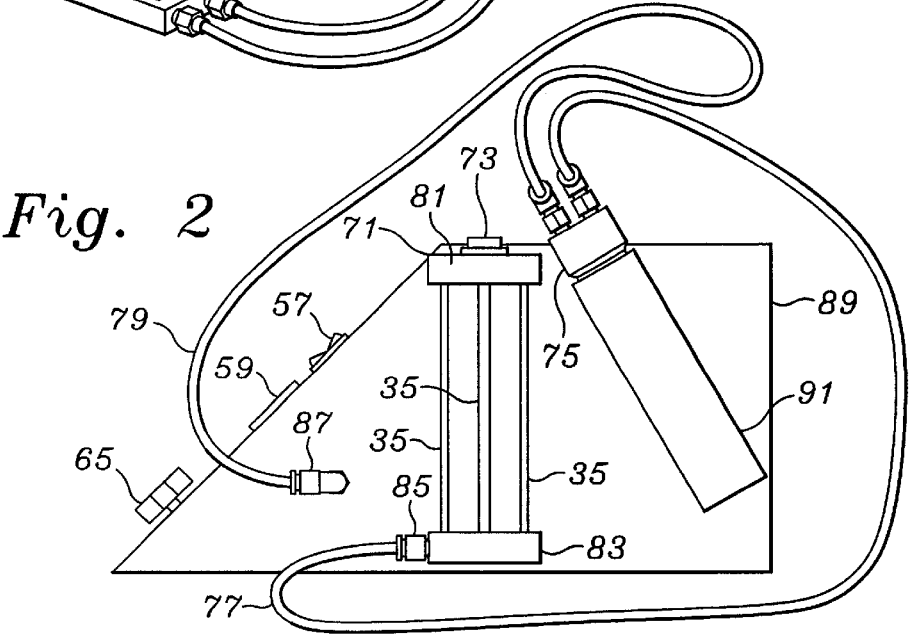
FIG. 2 is a plan right side view of system seen in FIG. 1 and illustrating the supply canister, and the manual application tool and vacuum/media line fitting.

Referring to FIG. 2, a right side view gives a better view of structures partially seen in FIG. 1, including the supply cannister 71. Supply cannister 71 also has a series of vertical supports 35, three of which can be seen in FIG. 2. The vertical supports 35 connect top plate 81 to bottom plate 83. The hoses 77 and 79 which lead away from the tool 75 connect with quick connect fittings to two different locations. Supply hose 77 connects to a quick connect fitting 85 connected to the bottom plate 83. Return hose 79 connects to a quick connect fitting 87 attached to a side 89 of the housing 23.

Side 89 of the housing 23 also supports a cylindrical support 91 which supports and protects the tool 75 within the support 91. The support 91 is in essence a stable holding holster in which a technician can place the tool 75 when the tool 75 is not in use. The use of a support will also promote gravity drainage of any particulate abraisive material which may have been located within the tool 75 at the time it is shut off.

Figure 3:
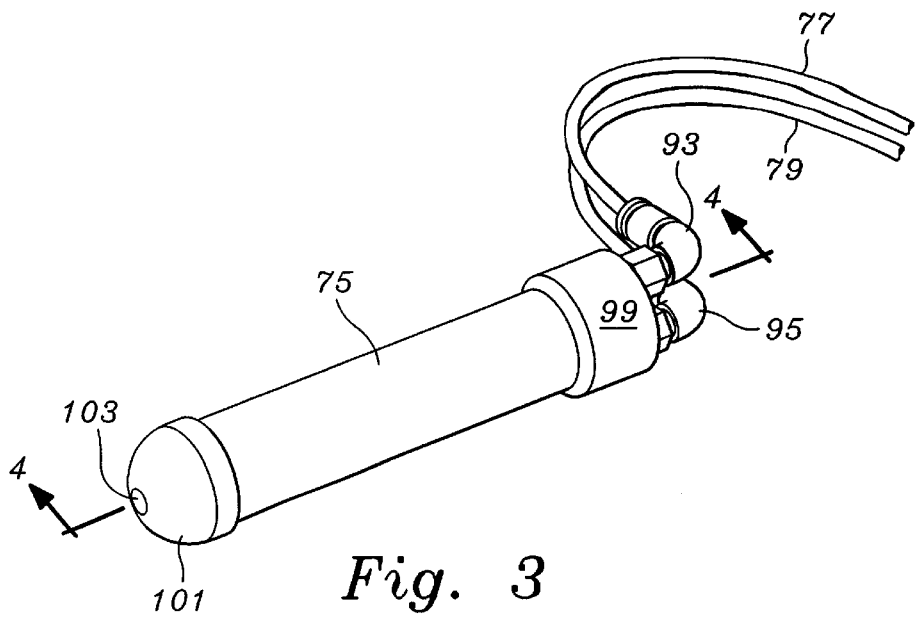
FIG. 3 is a perspective view of the handset illustrating supply and exit hose, and a removable plastic tip with a predetermined target aperture.

Referring to FIG. 3, a close up perspective of the tool 75 illustrates a better closeup of a pair of slip fittings 93 and 95, which connect the hoses 77 and 79. The tool 75 has a radially expanded portion 99 to accommodate the threaded fittings 93 and 95. Tool 75 has an elongate shaft to provide a length for acceleration of the abraisive particles in a geometry free of sharp turns to insure that the abraisive particles do not collect and can flow evenly toward a restriction to be shown. The end of the tool 75 is covered by a plastic cap 101. The cap 101 has an opening 103. In order for the system tooperate, the opening 103 must be covered t allow the vacuum to pass from non threaded bore 115 to bore 113 of manual contact tool 75. The opening 103 is placed directly over the area to be abraded. The hemispherical shape of the end of cap 101 facilitates the pencil like manual actuation over the area to be abraded. Other shapes can be used which may be more compatible with the structures to be abraded.

Even more importantly, the shape of the opening 103 can be adjusted easily by simply changing the plastic cap 101 having another, but different sized opening 103, possibly in conjunction to complementary structures elsewhere, to further control the shape and distribution of abraisive particles as they impinge on the target through the opening 103. The cap 101 is preferably plastic and disposable so that when the tool 75 is used to abrade skin, it can be disposed of to eliminate any contamination either through skin contact on the outside, or abraded skin particles which might be present inside the cap 101 such as adhering to the inside surface thereof.

Figure 4:
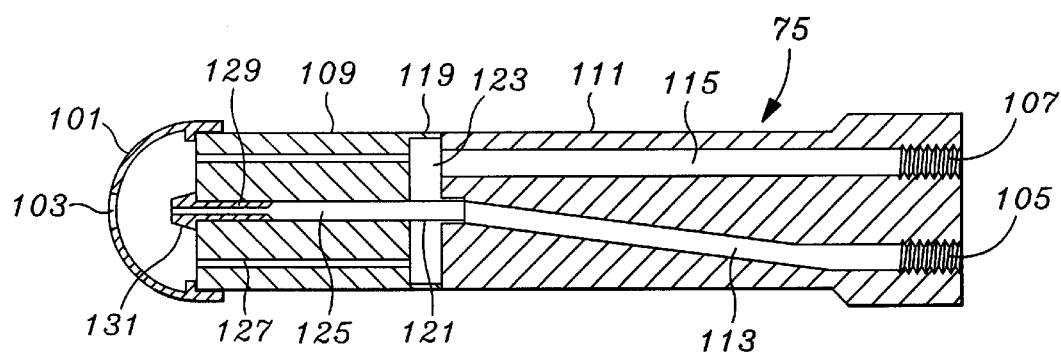
FIG. 4 is a sectional view taken along line 4—4 of FIG. 4 which shows the supply path and flow restrictor, and two of the radially located return channels which merge into a common channel connected to the return hose.

Referring to FIG. 4, a side sectional view of the tool 75 reveals a pair of threaded bores 105 and 107. When formed as a two piece structure, the tool 75 may have a front section 109 and a rear section 111. The formation as a section facilitates the formation of the bores within the tool 75 using simpler manufacturing methods, particularly since all of the bores seen in FIG. 4 have angular transitions or distribution points which would otherwise be difficult to achieve if formed as a single component.

Threaded bore 105 transitions to a non threaded section of bore 113 which angles toward the center of the rear section 111. The threaded bore 107 transitions also into a contiguous straight non threaded bore 115 and opens at the end of the rear section 111.

The front section 109 is formed with an outer axially raised rim 119 and an inner axially raised rim 121 which should be raised to at least the same extent as the rim 119 and preferably into the first portion of bore 113 for a good fit. However, an accommodation should be made so that the air and particles flowing through the bore 113 will not experience a reduction in cross sectional flow area. The raised rim 121 creates a chamber 123 which is in communication with the contiguous straight non threaded bore 115. With this configuration, the front section 109 can sealing attach to the outer periphery of the rear section 111 at the same time that the rim 121 surrounds the peripheral face of the rear section 111 immediately around the opening of the non threaded section of bore 113. This not only isolates and continues the channel of the non threaded section of bore 113 but insures that the annular chamber 123 is isolated between the rim 119 and the rim 121.

The front section 109 has a center bore 125 and a series of peripheral bores 127. The center bore 125 has a flow accellerator 129 which is seen as an annular insert 131. Flow restriction can be accomplished by making center bore 125 of two different internal diameters. However, the use of a separate flow accellerator 129 enables its removal should any unduly large particle block the entrance. The flow accellerator has a conical portion at its front end to set the extent of its insertion within the center bore 125. Other options include any type of venuri orifice or any structure which effectively boosts the velocity of the materials going through the opening. Both due to the fact that the tool 75 can be disconnected near its middle and that insert 131 is accessible from the end of the tool 75 makes removal of the insert 131 easy to accomplish.

In the normal operation, a fast stream of air or other fluid enters the threaded bore 105, possibly from the fitting 95 and hose 79. The fluid, preferably a gas, carries abraisive particles along with it. The gas and abraisive particles travel through the bore 113, across the inner axially raised rim 121 and into the center bore 125. When the flow accellerator 129 is encountered, the speed of the flow of the gas fluid speeds up to a high speed as it travels through the flow accellerator 129. The high speed fluid and abraisive particles exit the accellerator 131 and travel through the interval of space between the open end of flow accellerator 129 within the plastic cap 101 and toward the opening 103. Where the surface to be abraded is covered by the opening 103, a closed chamber is formed wherein the abraisive material which strikes the surface appearing in the opening 103 may then be urged into the series of peripheral bores 127, as well as the carrier gas and particles of material which have been abraded from the surface of the structure adjacent the opening 103. This enclosed process is expected to reach steady state quickly so that none of the abraisive particles nor the abraided material is expected to collect within the volume enclosed by the cap 101. Spent abraisive particles and abraded material travel through the peripheral bores and into the chamber 123 and then out through the non threaded bore 115, through attachment of slip fiting 93 to the hose 77. The mechanism to produce pressure and vacuum to insure steady state operation will be explained from a systems standpoint, below.

Figure 5:
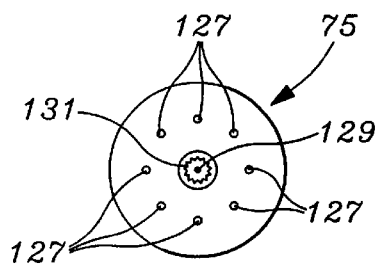
FIG. 5 is an end view of the handset with the plastic tip removed and looking into the supply path, flow accelerator, the radially located return channels.

Referring to FIG. 5, a front view of the manual contact tool 75 is seen, but without the presence of the plastic cap 101. The peripheral location of the entrances of the series of peripheral bores 127 are readily seen. The placement of the series of peripheral bores 127 is designed to make even availability of a return path for the spent abraisive particles and abraded material. It is understood that different sizes of plastic cap 101 and opening 103 can be used for different applications. The cap 101 can be made with the opening 103 closer to the open end of the insert 131 for more severe abraision, or it can be made with the open end of the insert 131 spaced significantly from an opening 103, perhaps even a larger opening 103. This arrangement would abrade at a slower rate, and over a wider area.

Figure 6:
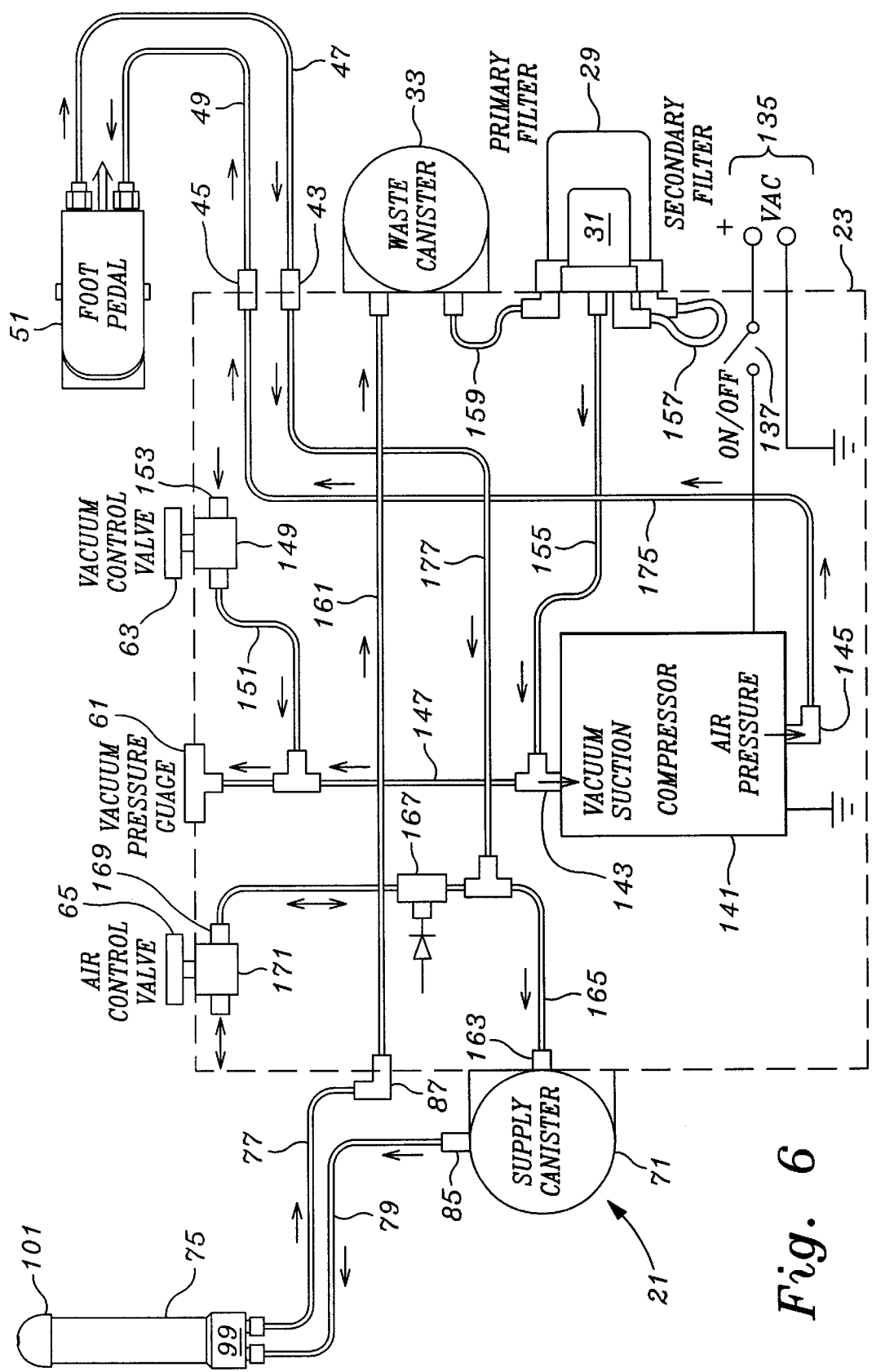
FIG. 6 is an overall schematic view of the first embodiment of the contained direct particle beam flow abrasion system and capable of any combination of vacuum or pressure boost operation.

Having now seen the external portions of the system 21, a further explanation of the workings of the system as a whole will facilitate a further understanding thereof. Referring to FIG. 6, a schematic view which is orientated with regard to a downward look onto the housing 23 from the rear is shown. In this way, a schematic explanation can be had with regard to the physical layout of the system 21.

Electrical power is provided to the system 21 with a regular wall outlet 135. An on/off switch 137 controls power availability into the housing 23, and may be key controlled in order to keep the system 21 from unauthorized useage. At the heart of the system 21, a combination vacuum pump and compressor is seen and hereinafter referred to as a vacuum pump/compressor 141 is seen. This device is typically available as a sealed unit with electric motor internally located and has a dual one way check valve arrangement creating a one way air flow action which sucks into at least one port 143 and produces a pressurized output through at least one port 145. Each half stroke of the piston produces a vacuum at port 143, while the next half stroke of the piston within the vacuum pump/compressor 141 produces a pressurized output at port 145. On the physical vacuum pump/compressor 141, ports which are not used may be simply plugged off.

The basic theory of operation with a single vacuum/compressor operating system is that "the motor will always operate with a constant load, and that load should be as small as possible". Keep in mind that the vacuum/compressor has a single piston operating within a chamber on one side of the piston, the face side. Each stroke of the piston which creates a displacement space in the chamber draws air into the chamber and resistance in the inlet line creates vacuum during this step. As the piston strokes back to reduce the volume of the displacment chamber, compression is created. Air for compression is based upon the air which entered the chamber and which was left over from the vacuum stroke, after the inlet valve closes just at the maximum of the vacuum stroke. Thus the reason that the load will not double is that under maximum vacuum load the compression load is naturally near zero. The maximum compression load can only occur when maximum air intake into the compressor/pump occurs when essentially no vacuum occurs, when the vacuum inlet is at atmospheric pressure.

Thus, the vacuum or air section of the vacuum compressor/pump 141 should never otherwise be restricted in any way. The system 21 of the invention uses the vacuum and air control valves as shunt units and not positive control valves which either purposefully starving the vacuum inlet to the compressor/pump 141 or purposefully holding back a buildup of pressure from the outlet of the compressor/pump 141.

The Explanation will begin at the suction port 143, since the system 21 can operate in a vacuum mode only without the pressure boost from the port 145. The vacuum port 143 is connected to the pressure guage 61 seen previously in FIG. 1, through a line 147. The pressure guage 61 simply gives an indication of the degree of vacuum being developed at the vacuum port 143. A "T" connection connects the line 147 between the pressure guage 61 and the port 143 to one side of a vacuum control valve 149 through a line 151. The vacuum control valve 149 is a through valve having a fritted or filtered port 153 for which fluid communication is controlled to selectively bleed air into the vacuum line 151. When vacuum control valve 149 is closed, no air flows throughthe vacuum control valve 149, and the pressure guage 61 is enabled to develop as much vacuum as the system 21 will otherwise allow based upon flow availability and other factors to be discussed. When the valve 149 is opened, air which passes through the filtered port 153 as well as air from the remaining parts of the system 21 combine to lower the vacuum at port 143 and which is read at pressure guage 61.

Port 143 has a "T" connection which is shown adjacent to the vacuum pump/compressor 141 as line 155. Line 155 is connected into the secondary filter 31 which is shaped as a cylindrical filter. The line 155 is connected to the secondary filter 31 output. The input to the secondary filter 31 is a connecting line 157 which connects to the output of a primary filter 29. The input of the primary filter 29 is connected to the output of waste cannister 33 through a line 159.

The waste cannister 3 has a knock-out grid to help separate the abraisive material, which in small sizes can be very light and difficult to separate from the stream of flowing air. A knockout grid deflects incoming abraisive material, enabling it to drop to the bottom of the waste cannister 33. When skin is abraded, the waste cannister 33 may also have a dye or other security device to insure that users will not attempt to re-use the contaminated abraisive material.

The waste cannister 33 has an input connected to a line 161 which is connected to the quick connect fitting 87 through the wall of the housing 23. As before, quick connect fitting 87 connects to hose 77 and receives the return air, spent abraisive material and abraded material from the abraision reaction within the plastic cap 101.

Again considering the manual contact tool 75 and working in reverse, the hose 79 brings the abraisive material and air from supply cannister 71. Cannister 71 has a quick connect fitting 85 leading to a vertical tube witin the cannister. The vertical tube has a hole near its bottom extent. As air enters the cannister, either by negative pull from the vacuum or positive air boost pressure, or a combination of both, it flows through the top of the vertical tube. As the air passes the hole near the bottom extent of the vertical tube, abraisive material is drawn through the hole in a proper flow amount. The size of the hole enables control of the air and abraisive mixture.

The supply cannister 71 has an input port 163 connected to a tube 165. The line 165 is connected through a "T" shaped pressure difference inlet check and relief valve 167, which leads to a first port 169 of an air control valve 171. The relief valve 167 will allow air into the line 165 upon the existence of a pressure differential of about 0.5 inches of mercury between the pressure in lane 165 and atmospheric. The inlet of the relief valve is from the ambient surrounding or through a filter.

Since an explanation should be given first of the simplest system, the vacuum only system will be explained. From the operator's perspective, the valve handle 63 of vacuum control valve 149, in order to direct air into the vacuum side of the vacuum pump/compressor 141, is set to full open to insure that operation starts off at a minimum level. Valve handle 65 of air control valve which is in communication with and lets air into the supply canister 71, is set to full open, and the foot pedal control 51 is left un-actuated to shunt pressure through its vent. The manual contact tool 75 has the plastic cap 101 in place, with its opening 103 occluded over the area to be abraded in order to help develop vacuum and to make ready for abrading a surface to be abraded.

The valve handle 63 of vacuum control valve 149, is turned in order to begin to starve ambient air from entering into the vacuum side of the vacuum pump/compressor 141. As this begins to occur, the vacuum developed at the tip of the manual contact tool 75 will be felt through the system 21 at the downwardly extending, "U" shaped venturi tube 275 (see FIG. 11) of the supply canister 267. Air will be drawn through the vacuum relief valve, if necessary; through tube 165 and into the bottom of the supply canister 267. The introduction of air into the bottom of the canister 267 is through a structure designed to distribute the air through the media used for abrasion to "excite" the media, keep it from clumping and to keep it fluidized. Air passes from the bottom of canister 271, between and through the fluidized mass to the top of "U" shaped venuri tube 275, then picks up media as the air passes through the tube 275 and flows past the small inlet orifice 277. The abraisive media is carried along in the tube 79 on its way to the manual contact tool 75. In the manual contact tool 75, the flow accellerator 129 increases the speed of the abraisive media and air stream to its maximum velocity and energy as it exits the end opening of the annular insert 131. Once the high speed mixture of abraisive media and air leave the annular insert 131, it is directed as a particle beam aimed at the opening 103 of the cap 101 to directly strike any surface exposed within the opening 103.

If one parameter in the conditions is changed, overall operation is changed. In "vacuum only" operation, as illustrated above, if the inlet/outlet control valve 171, in communication with supply canidter 71 is set to a closed position (full on for air boost operation) to shut off the supply of ambient air to the supply canister 71, and when this occurs in the absense of an air boost from lines 47 and 49, a vacuum relief valve 167 opens to supply air to the vacuum tube 165 for still permitting operation. The system will, but with a loss of 0.5 inches of mercury due to the pressure drop at the relief valve 167.

Referring again to FIG. 6, the system 21 includes a pressure boost using the pressure port 145 of the vacuum pump/compressor 141. When the boost is operated, the response to the system 21 from opening and closing the valves 149 and 171 is different. Port 145 of the vacuum pump/compressor 141 provides compressed air through a line 177 to the slip fitting 45. A hose 49 connects the slip fitting 45 to foot pedal 51, which is a convienient quick-open/quick-close vent valve. The output hose 47 provides pressurized air in response to operation of the foot pedal 51.

Given that the vacuum pump/compressor 141 may be positive displacement, there are two control possibilities for operation. In one configuration, a constant pressure relief valve is placed in the foot pedal control 51 to keep the supply pressure high and constant. In this configuration, when the foot pedal control 51 is activated, the normally closed valve in the foot pedal control 51 is opened to supply hose 47. However, this is not the preferred mode of operation. If the presssure were allowed to build, the speed of the drive motor within vacuum pump/compressor 141 would begin to slow down as it works against ever higher pressures, and which would perform more work to provide a high pressure flow of air through a high pressure relief valve. In such a case, the foot pedal would be depressed to open flow into hose 47.

However, to save energy and provide for vacuum pump/compressor 141 to expend the bulk of the energy from its motor in creating vacuum until and when the pressure boost is needed, the foot pedal valve 51 is connected in the opposite sense. When undepressed, the foot pedal valve 51 is in the open position, and the exit port is provided with a filter or diffuser so that air entering from line 175 and hose 49 flows constantly at high volume and low pressure to the foot pedal control valve 51 and out through a diffuser. The diffuser can be selected based upon the pressure drop that it will present, along with the line 175 and hose 49, virtually no pressure drop to the pressurized air. When the foot pedal control valve 51 is depressed, the pressurized air, instead of escaping to the surroundings, is redirected through the hose 47 as the escape is shut off and the passage to the hose 47 is opened. In this configuration, pressurized air is supplied at about the moment when the ability of the vacuum pump/compressor 141 to create high vacuum would normally be compromised. The boost provided is effective regardless of the exact magnitude of the vacuum and pressure boost, since an effective boost can be considered as a pressure differential applied at the manual contact tool 75.

Pressurized air flowing into quick connect fitting 43 also flows into a line 177 which is connected by a "T" connector into line 165. The additional pressure applied to line 165 now increases the driving force applied to the supply cannister 71 and manual contact tool 75. Now, pressurized air is applied upstream forcing air and abraisive material toward the target at the opening 103, while a vacuum drives the removal of spent abraisive and abraded material. Under purely vacuum operation, the operating differential included any vacuum in line 77 working against atmospheric pressure minus any pressure drop in the air entering through the combination of relief valve 167 and or valve 171. Under pressure boost conditions, essentially the same vacuum conditions are present, but the increase in the inlet operating pressure is responsible for the increase in driving force of the flow of air and abraisives.

Looking again at valves 149 and 171, it is clear that their operation is different under conditions of pressure boost. Maximum operation under vacuum only (no shunt into the vacuum line to reduce the vacuum) involves the closure of valve 149 and that valve 171 be completely open (full shunt, no air boost). However, when pressure boost is applied through line 177, increasing air pressure will reverse the flow of air through the valve 171. Thus, the most powerful operation under conditions of power boost occur when valves 171 and 149 are closed. In this high power setting, foot pedal control valve 51 is used to supply very controlled high pressure blasts of air and abraisive to the manual contact tool. With valves 171 and 149 closed, the only inlet air will be through the relief valve 167, with no air boost applied. When pressure boost is applied, and since the relief valve 167 is a one way check valve, it shuts instantly. Thus the system 21 of FIG. 6 is then set to operate between a minimum flow with incoming air entering through relief valve 167 and maximum boost pressure and vacuum as relief valve 167 shuts. It would be preferable, in intermittent, foot controlled power boost operation to completely shut off the flow of air through the supply cannister 71, but too high a vacuum might build, especially if cap 101 is used over skin, and the provision of the relief valve 167 is a safety feature.

From a setting of maximum power boost described, the opening of valve 171 will both dampen and narrow the operating range of system 21. As the valve 171 is opened, the vacuum operation is increased. When the foot pedal control valve 51 is opened, much of the flowing air escapes through the valve 171 which reduces the pressure power delivered to the manual contact tool 75. Thus the opening of the valve 171 brings operation from between states of maximum power to minimum power operation with the foot pedal control valve 51, to a state of, for example ⅔ maximum available power to ⅓ maximum available power operation. When the valve 171 is completely open, the power operation will achieve a minimum range between maximum and minimum power operation.

Opening of the valve 149 can reduce the amount of vacuum, and thus move the midpoint range of operation when used in conjunction with valve 171. However, in general, not as much advantage is believed to be derived from opening the valve 149 during power boost operation. In addition, if enough of the vacuum is shunted with valve 149, there may be insufficient vacuum to pull away and collect the spent abraisive and abraded material.

System 21, without any boost input from hoses 47 and 49, is a Shunt Vacuum/Air Controlled System. As such the maximum control of the vacuum and air utilized within the system is, from an energy standpoint, from approximately "full on" to "half on" with no significant real control below these levels even though through manipulation of the valves it will appear that the vacuum and air can be turned "off". This is only an appearance, in vacuum only operation the vacuum control valve 153 only has significant effect on operation within about 20 degrees of rotation of the control valve 153 from maximum. This characteristic has led to the design of special control valves for controlling the vacuum and boost air.

Another characteristic of system 21 is that when the system 21 is used with the "air boost" and the foot pedal control 51 pressed to enable the boost, the system 21 can and will blow abrasive media out through the opening 103 of the manual contact tool 75 without any material occluding the opening 103 or lying idle to the side of opening 103 within cap 101. The use of the foot pedal control 51 poses a risk of discharging media inadvertantly into an area that should not be bathed with abrasive material. Also, if the manual contact tool 75 is removed from coverage of the opening 103 from a position over the material to be abraded prior to releasing the foot pedal control 51, abrasive media will likely be discharged out of opening 103 of the manual contact tool 75 and can cause harm to the material and the area outside of the area being abraded.

The control over the air boost in FIG. 6 is based upon softening the effect of a surge of boost air upon operation of the foot pedal. The earlier mentioned use of a limit valve, such as valve 331 of FIG. 18 in place of the foot pedal control 51 contemplates either removal or non-operation of the boost air control valve. There is not a point in providing smooth controllable flow such as with a valve 331, while blunting the control with an air control valve 65. In FIG. 6, removal of the foot pedal control 51, and replacing with valve 331, and eliminating and closing off the air control valve 65 and its line will enable measured control, but will eliminate the ability to provide a quick on/off boost.

In addition, system 21 does not provide a user friendly method or structure for secure collection for the waste media and abraded material mixture (previously used) drawn from the manual contact tool 75. The supply of used media may be improperly poured into the supply cannister by an operator, which could in fact contaminate the supply media, or the waste media could be drained out of the bottom of the waste cannister by the operator. This would allow the operator/owner the option of reusing the same contaminated abrasive media by recycling it back into the supply cannister 33 or discarding the used media with possible contamination from the abraded area in the form of abraded material in an unsafe and uncontrolled manner.

When used in a medical environment, system 21 described thus far does not address the issue of sterile air flow leading to the incorporation of 0.7 micron filter upstream of the boost air system, a ceramic oven for and ultaraviolet decontamination system for air circulating in the system 21. Deep abrasion of human tissue might create germicidal and other contaminants which might otherwise circulate in the system 21.

System 21 works well as it is described, and the aforementioned and aftermentioned considerations only relate to specialized environments in which abraision may be performed, and in which other considerations need to be taken into acount, those considerations not addressed by system 21. Where system 21 is used for simple etching, for example glass or other media for which recycling is acceptable, the system 21 forms an efficient, neat, clean system. For example, where a system 21 is purchased and used by a single same owner, in a shop setting for cleaning or abrading small parts, the lack of controls over the disposition of the supply and waste abraisive is not expected to be a problem.

These characteristics of System 21 do not pose a problem for most general applications. Other applications may have a more refined set of needs and caused further invention as an effort to design and develope a new and better flow control system, air boost control system and media supply/waste control management system and air purification sterilization.

Figure 7:
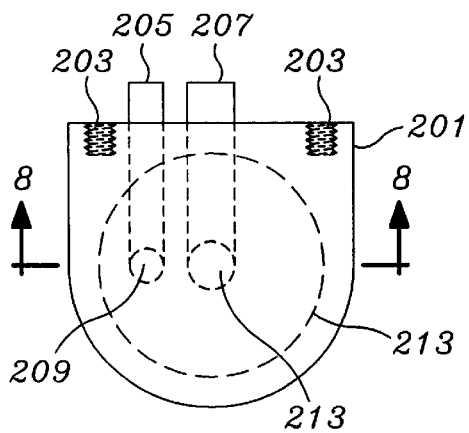
FIG. 7 is a top view of an alternative waste canister system illustrated as a screw type vertically depending from a top plate from which it is difficult to remove spent abrasive material.
Figure 8:
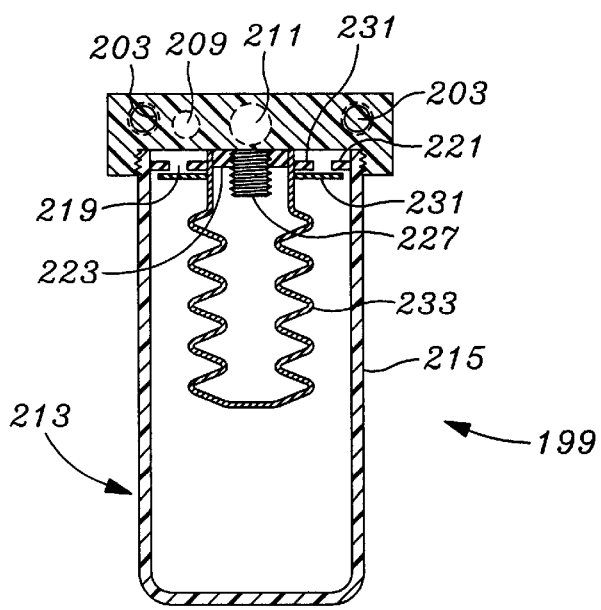
FIG. 8 is a lateral sectional view of the alternative waste canister system illustrated in FIG. 7.
Figure 9:
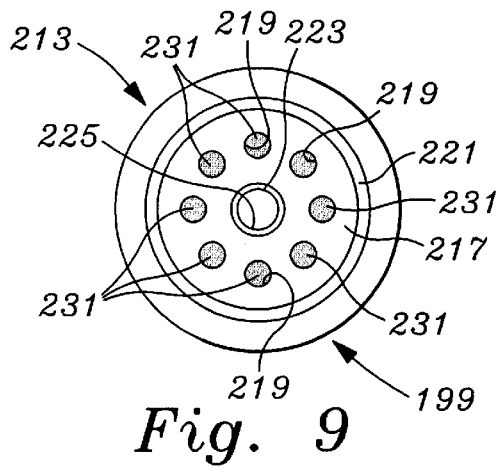
FIG. 9 is a top view of the disposable wast canister seen in FIG. 8.

Referring to FIGS. 7, 8, & 9, an alternative waste cannister system is illustrated as a screw type in which it is difficult to remove spent abraisive material. A waste cannister assembly 199, similar to waste canister 33, includes a top plate 201, similar to top plate 37, has a pair of threaded bores 203 for bolting onto to the housing 23. The top plate 201 has a pair of tubes extending therefrom, including entrance tube 205 and exit tube 207. The tube structures have bores 209 and 211 which extend toward the middle of the top plate 201 and then are directed downward. As the tubes extend inward to the middle of the top plate 201, they may exist as tubes affixed to the bottom of the top plate 201, or as bores into a solid body of a top plate 201.

In either case, the change in direction helps in separating the abraisive material from the gas stream. In the top plate 37, for example, a 3-dimensional mesh grid was used to change direction. The same principle is used here, as will be seen. Gas, spent abraisive and abraded material enter the entrance tube 205 and is directed downward. After negotiating structures to be shown, the exit gas which has been filtered, preferably with a 5 micron filter, enters the bore 211 and exits the exit tube 207. Also seen in dashed line format is the placement of a collection cannister 213 which is supported and sealably engaged.

Referring to FIG. 8 a sectional view taken along line 8—8 of FIG. 7 is a view looking into the collection cannister 213 illustrates the component parts thereof. Cannister 213 has a metal or plastic outer wall 215 and a top plate 217 into which a series of peripheral holes 219 are punched or bored. An outer ring seal 221 seals the cannister 213 against the top plate 201 to insure that none of the spent abraisive nor abraded material escapes. An inner ring seal 223 isolates a threaded center bore 225 of the canister from the series of peripheral holes 219. Thus, the material entering through bore 209 hits the top plate 217, and falls through the peripheral holes 219 and into the space bound by the outer wall 215. Outer ring seal 221 prevents any of the entering material from escaping from the canister 213. Inner ring seal 223 isolates the entering material from contacting the exit air stream to be filtered.

As can be seen, the bore 211 terminates in a threaded nipple 227 which threadably engages the threaded center bore 225. In this configuration, the cannister can be threadably unscrewed from the threaded nipple 227 to be easily changed. Circumferentially extending around beneath the top plate 217 is a rubber flapper 231. Rubber flapper 231 bends downward to give way to the entering air stream, its spent abraisive material and abraded material.

Once the abrasion material and abraded material enter the canister 213, a filter 233 presents an expanded surface area through which the air may freely pass while leaving the solids behind. Even was the canister begins to fill, there is enough surface area of the filter 233 that flow should not be impeded. In addition, some flow can occur through the spent abrasion material once the level has become higher than the filter 233. In addition, to the extent that the abraded material is smaller than the abrasion material, much of it may be expected to collect at the bottom of the canister 213.

The flapper 231 provides additional passive structure to help separate the air from solid material, and also provides for sealing the internal contents of the canister 213 when air is not flowing through it. Once the abrasion process is stopped, the system 21 can be purged with air, or simply have the supply of abrasion material stopped or allow it to be exhausted. This would clear the abrasion material from the system 21. When the system 21 is shut down, the canister 213 can be unscrewed from the nipple 227 without any random material lying atop the top plate 217. In the best operating example, and since the volume of abraded material is expected to be slight with regard to the volume of abrasion particles, a supply canister would be provided having a known quantity of abrasion material. When the material is depleted, the system 21 will sweep itself clean, and it will then be time to change the waste cannister 213 and add a new supply canister.

Referring to FIG. 9, details of the top of the canister are shown. Structures which can be seen include top plate 217, its series of peripheral holes 219, the outer and inner ring seals 221 and 223, threaded center bore 225 which engages the threaded nipple 227, and also the rubber flapper 231 which can be seen through the series of perhiperal holes 219.

Figure 10:
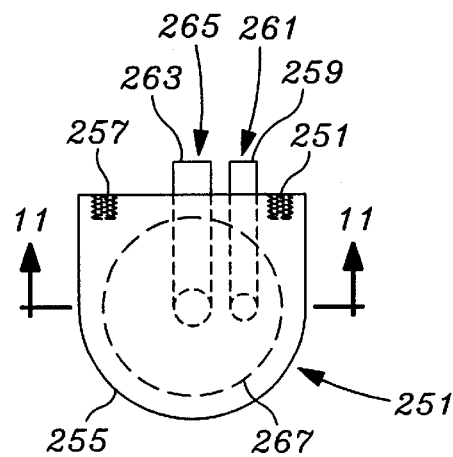
FIG. 10 is a top view of an alternative supply canister system also illustrated as a screw type vertically depending from a top plate.

Referring to FIG. 10, a supply canister assembly 251, similar to the supply canister assembly 71, is illustrated as having a top plate 255 having a pair of blind threaded bores 257 to facilitate connection to the housing 23. An air inlet tube 259 provides an entrance into an air inlet bore 261 which extends into the body of the top plate 255 either as a continuous tube, or as a bored out volume. An air outlet tube 263 provides an exit from air and abraisive outlet bore 265 which extends into the body of the top plate 255 either as a continuous tube, or as a bored out volume, and which carries a stream of air, along with abraisive material. The outline of a supply canister 267 is shown in dashed line format.

Figure 11:
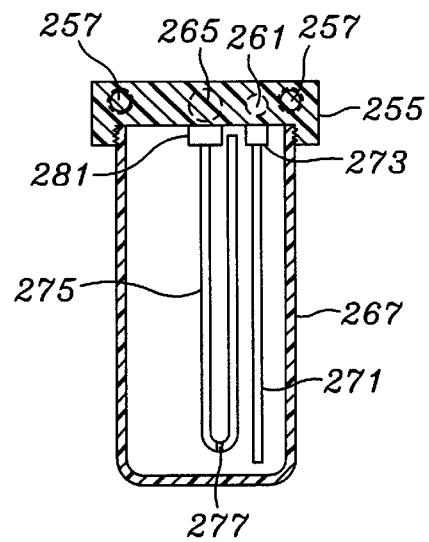
FIG. 11 is a lateral sectional view of the alternative supply canister system illustrated in FIG. 10.

Referring to FIG. 11, a sectional view taken along line 11—11 of FIG. 10 illustrates the internal structures of the supply canister assembly 251. The internal structures can be provided as structures permanently fixed with respect to the top plate 255 or detachable as by threaded engagement. In communication with air inlet bore 261 is a downwardly extending puffer tube 271. The puffer tube 271 causes inlet air to exit at the bottom of the supply canister 267 to introduce a fluidizing action on the particulate abraisive material wihtin the canister 267. This insures that the abraisive material will always remain free flowing, loose and will not clog or block the feed exit. The puffer tube 271 is shown as having an upper expanded portion 273 which is preferably a threaded fitting for engagement with a matching threaded fitting in the top plate 255.

To the left of the puffer tube 271, with respect to the view of FIG. 11, and in communication with the air and abraisive outlet bore 265 is a downwardly extending, "U" shaped venturi tube 275. Venturi tube 275 has a small inlet orifice 277 at the bottom most portion of the "U" shaped bend which pulls in the abraisive material. For abraisive media having a size range of from 50 to 100 microns, a suitable size for the inlet orifice 277 is about 0.045 inches in diameter. The selected size for any application will be a function of the size of the abrasive media and the amount of media to be applied to the surface to be abraded relative to the size of the abrasive media.

The venturi tube 275 has an open end 279 which terminates at the end of an upward extent of the tube 275 generally parallel to the downward extent from a fitting 281. The open end 279 draws air which has percolated up through the abraisive material from the lowermost extent of the puffer tube 271. As the air rushes through the venturi tube 275, it causes the abraisive material to be evenly brought through the inlet orifice 277 to create an even air-abraisive material mixture which flows out of the air outlet tube 263 on the way to the manual contact tool 75.

Figure 12:
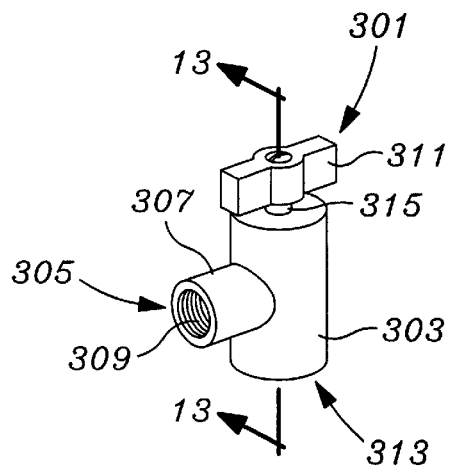
FIG. 12 is a perspective view of a cylinder element valve having a single boss and advantageously configured for use with the contained direct particle beam flow abrasion system vacuum control to linearize operation of the system to facilitate proportional analog control by an ordinary operator thereof.

Referring to FIG. 12, a simplified perspective view of a vacuum shunt valve 301 is seen, as one possible configuration of valve to be used for the vacuum control valve 149 of FIG. 6. Vacuum shunt valve 301 has a main body 303 having a side port 305 including a boss 307 with a threaded internal surface 309. A handle 311 is provided as a generally linear knob extending both directions away from a center pivot. Valve body 303 has an underside opening 313 indicated by an arrow, and the handle 311 is connected to the internals of the vacuum shunt valve 301 by a valve stem 315. It is understood that a vacuum shunt valve 301 can have 2, 3, or more bosses 307, each of whcih has an opening into the central part of the vacuum shunt valve 301 of a given size and shape. Bosses which are not utilized can simply be plugged off. Also, it may be preferable to limit the turning of the vacuum shunt valve 301 when installed for use with the system 21 in order to use the position of the handle 311 as an analog visual indicator for the level of operation of the vacuum shunt valve 301.

Figure 13:
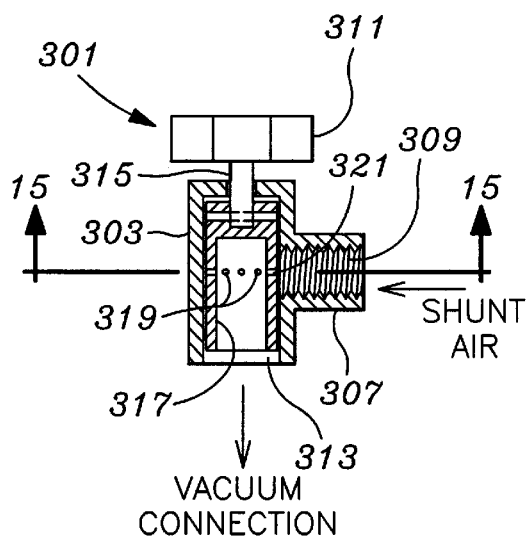
FIG. 13 is a side sectional view taken along line 13—13 of the valve of FIG. 12 and which illustrates the structure and operation thereof.

Referring to FIG. 13, a side sectional view taken along line 13—13 of FIG. 12 indicates the operation of the vacuum shunt valve 301. The valve main body 303 opening 313 in the bottom of vacuum shunt valve 301 is situated such that vacuum pressure can enter an aligned open end of a cylindrical valve element 317 before drawing permitted air to flow through a threaded internal surface 309 of boss 307. Note that the inside of cylindrical valve element 317 contains a series of miniature bores 319 which are shown as being roughly vertically centered in the threaded bore 309. As will be seen, the miniature bores 319 are distributed about the radius of the cylindrical valve element 317 and extend through the walls thereof. At the innermost end of bore 309, the bore 309 presents a window opening 321, exposing an area of the external surface of the cylindrical valve element 317 to the bore 309. This area of the bore 309 is emphasized as a window opening 321 because it is the view window of the external surface of the cylindrical valve element 317 which is important rather than the overall diameter of the boss 308 since the window opening 321 may be large, leading to a smaller diameter bore 309, or the window opening 321 may be small leading to a larger diameter bore 309. Further, there may be other sealing structures within the bore 309 which define a smaller or larger window, or which may define a different shaped window opening 321. It is the size and the shape of the window opening 321 which will determine which one or ones of the miniature bores 319 will be in the window opening 321 and therefore open to pass air flow within the bore 309, thereby shunting air into the applied vacuum in a linear manner.

In addition to considering window opening 321 as a static principle, add the motion of the cylindrical valve element 317 and the placement of the miniature bores 317 to create an ever changing multiple combination or "mix" of number and size of miniature bores 317 which pass across the window opening 321. As one of the miniature bores 317 approachs the edge of the window opening 321 it begins to move behind the edge of the window opening 321 and have its flow begin to be restricted. This may occur as another one of the miniature bores 317 approachs the opposite edge of the window opening 321 from a closed state and begins to emerge from behind the edge of the window opening 321 and have its flow begin to be opened.

This differential flow orifice principle is utilized herein to achieve a controlled flow evenly across the range of flow to which the valve is to be subjected. Because fluid flow, such as air is very non-linear, a valve opening profile which is percentage proportional to the area available for flow simply will not yield the linearity needed, it is ineffective. Where a valve with significant capacity is used, linearizing the lower end of its operating range would normally require an expensive controller, with an extra fine angular discrimination. However, the inventive use of a series of exactly spaced miniature bores 319, and which are spaced to frame in and frame out of the window opening 321 as the valve handle 311 is turned will yield a linearization of valve flow, and which is proportional to the angular displacement of the valve handle 311 and stem 315. This enables the physical position of the valve handle 311 to be used as an analog flow indicator and the housing of the system 21 or any improvements thereof may bear an indication of flow, against which the position of the valve handle 311 can be compared. This enables the operator to have better absolute and reproducable control over the flow, and to verify the flow through visually checking the position of the valve handle 311. This advance in the valve art is particularly significant for the linearization of the lowest portion of the flow spectrum. Although not shown in FIG. 13, it is prefaerable that the vacuum shunt valve 301 be provided with a stop to insure that the displacement can occur over a 180° range only, although since the flow is from the port 309 of the valve through the valve main body 303 exiting bottom opening 313, and since only one boss 307 is used as an inlet, the extent of the radial distribution of the miniature bores 319 across the face of the cylindrical valve element 317 could be made to exceed 180°. For example, in an extreme case, and where the window opening 321 occupied 20° of the area of the cylindrical valve element 317, a series of miniatures bores 319 could be distributed over the remaing 340° of the cylindrical valve element 317. The limitation of the vacuum shunt valve 301 to 180° is to make certain that the readings for the operator's use are always above the valve handle 311 so that the operator will not have to stoop or bend down to read indicator marks under the handle 311.

Figure 14:
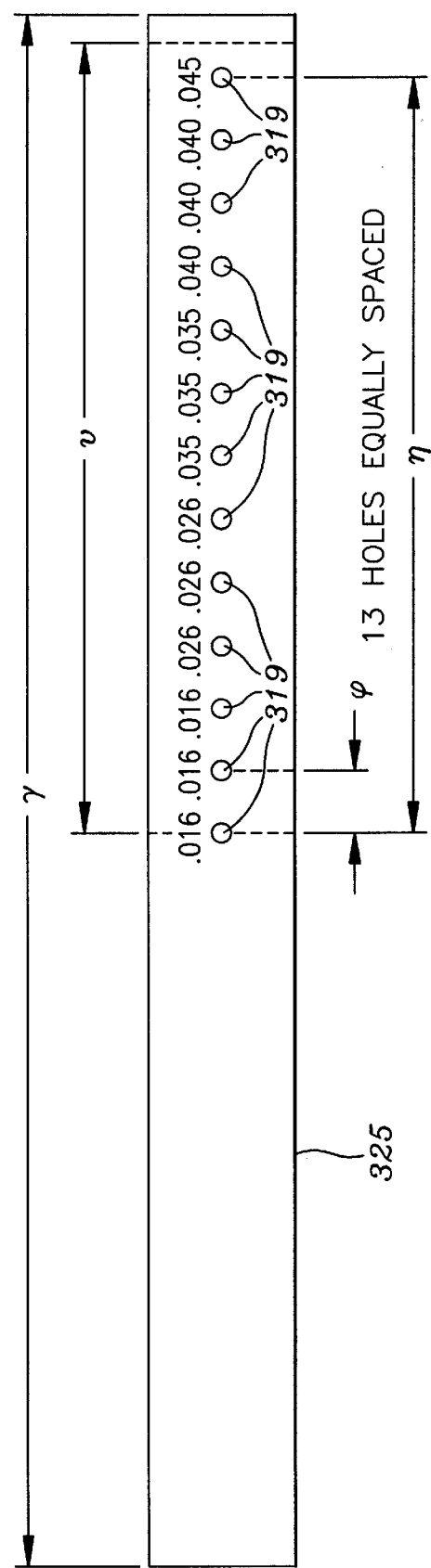
FIG. 14 is a linearized representation of the location of various sized and placed flow apertures on the cylinder element of the valve of FIGS. 12 and 13.

Referring to FIG. 14, a linear illustration of the placement of the miniature bores 319 on the cylindrical valve element 317 is illustrated. The parameters of this drawing are by way of example only and depend heavily upon the geometry of the cylindrical valve element 317, including its diameter, height, and the area of the window opening 321. In this case, the window opening 321 is based upon a 0.355 inch diameter internal diameter against the cylindrical valve element 317 to form a saddle window. The cylindrical valve element 317 is about 0.75 inches in diameter. As can be seen, a large diameter valve element 317 with a small diameter window opening 321 would create the possibility for many more individual combinations of miniature bores 319 in the window opening 321.

Given that the vacuum shunt valve 301 is desired to provide operablility over 180° of its range, it can be seen that the miniature bores 319 roughly occupy a little less than half of the linear length of a linear representation of cylindrical valve element 317, which is numbered as 325. The overall length of the linear representation 325 is shown as γ the roughly 180° operating range of the linear representation 325 is indicated with the symbol ν. The miniature bores 319 are fairly equally spaced at about 15° each, with there being from one to three of the miniature bores 319 being in the window opening 321 at any given time. The miniature bores sequentially occur across the linear representation 325 and have a diameter of 0.016, 0.016, 0.016, 0.026, 0.026, 0.026, 0.035, 0.035, 0.035, 0.040, 0.040, 0.040, and 0.045, inches in diameter. The center to center spacing of the first and last miniature bores 319 is shown as being η, and the hole spacing of about φ° which, given the dimensions of the window opening 321 and diameter of the cylindrical valve element 317, is expected to be about 15° apart.

From a position of fully closed, the window opening 321 would first begin to partially open the first 0.016 inch miniature bore 319 and then fully open the first 0.016 inch miniature bore 319. As the cylindrical valve element 317 continues to turn, the second 0.016 inch miniature bore 319 comes into view of the window opening 321 adding more air flow (more shunt). Finally, the third 0.016 inch miniature bore 319 comes into view of the window opening 321 adding still more flow. Next, as the first 0.016 inch miniature bore 319 begins to move out of view or presence within the window opening 321, it is replaced by a first 0.026 inch miniature bore 319. The last 0.016 inch miniature bore 319 is thus "exchanged" for the first 0.026 inch miniature bore 319 to thus slightly and linearly add more flow. As the cylindrical valve element 317 continues to turn, the second 0.026 inch miniature bore 319 comes into view of the window opening 321 as the second 0.016 inch bore leaves the window opening 321, to thus slightly and linarly add more flow through the vacuum shunt valve 301. Finally, the third 0.016 inch miniature bore 319 comes into view of the window opening 321 as the third 0.016 inch bore leaves the window opening 321, again slightly and linarly add more flow through the vacuum shunt valve 301.

Next, the first 0.026 inch miniature bore 319 begins to move out of view or presence within the window opening 321, it is replaced by a first 0.035 inch miniature bore 391 and the process is repeated. At the end, a 0.045 inch bore is added as a 0.040 inch miniature bore 319 is eliminated.

For optimum smoothness, any two miniature bores which are being "exchanged" should have their respective beginng exits and entry into the window opening 321 occur simultaneously. Otherwise, there would be an undesired fall in flow immediately following a rise in flow, and linearity would be compromised.

Further, it is discovered that the valve 301, and similar valves having a cylindrical valve element hereinafter described, have a direct scalability to higher volume flow. Doubling the dimensions of the valve 301 doubles its flow ability and capacity. As such, the dimensions given above coule be applied to different sized valves 301 to enable the systems described in the embodiments of the invention to be scaled according to size, with no experimentation needed.

Figure 16:
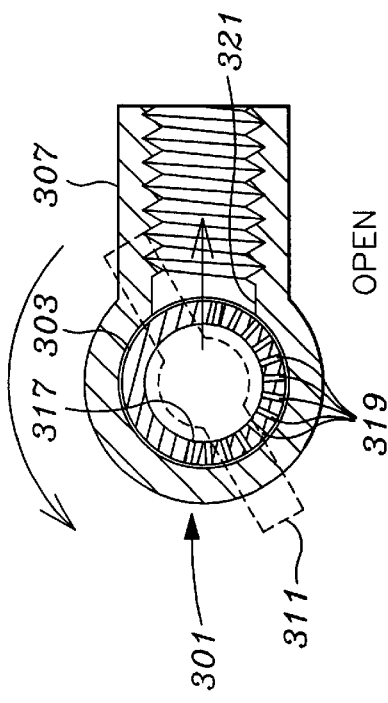
FIG. 16 is a view similar to that of FIG. 15 and showing angular displacement of the cylindrical valve element of the valve of FIGS. 12–15 as it is operated.
Figure 15:
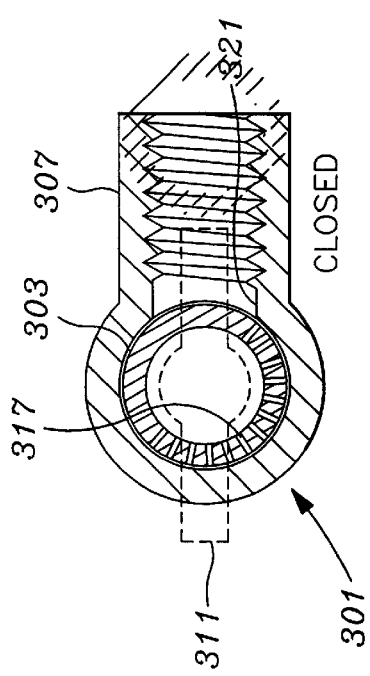
FIG. 15 is a view taken along line 15—15 of FIG. 13 and illustrating the position of the cylindrical valve element of the valve of FIGS. 12–14 as it is operated.

FIG. 15 is a sectional view of the vacuum shunt valve 301 taken along line 15—15 of FIG. 13 and which illustrates the position of the miniature bores 319 when the valve is in the closed position. FIG. 16 illustrates initial movement of the cylindrical valve element 317 bringint the first three 0.016 inch diameter miniature bores 319 into view of the window opening 321.

Figure 17:
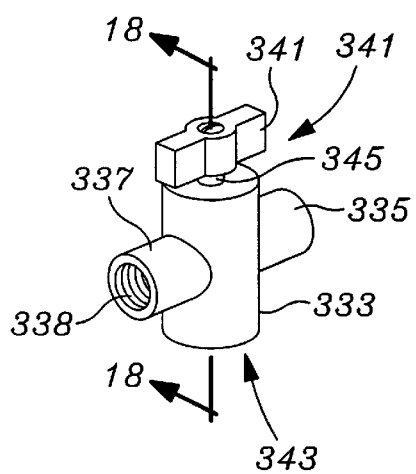
FIG. 17 is a perspective view of a cylinder element valve having a pair of oppositely disposed bosses and advantageously configured for use with the contained direct particle beam flow abrasion system to linearize operation of the system air boost control to facilitate proportional analog control by an ordinary operator thereof.

Referring to FIG. 17, a simplified perspective view of a positive feed diversion air valve 331 is seen, as one possible configuration of valve to be used for replacement of the foot pedal control 51, or in some instances used in conjunction with any sort of hand tool or any sort of foot control boost, in providing air boost to the system 21, and which will be more advantageously described and utilized in a further embodiment of the system of the present invention, below. It is introduced as a possible replacement for the foot pedal control 51 to illustrate its use in the system 21 thus far described with respect to FIG. 6. Positive feed diversion air valve 331 has a main body 333 and has a pair of side bosses 335 and 337 each of which has an open bore 338 and which may be threaded. The bosses are located 180° apart so that supply air may be split in two directions. A handle 341 is provided as a generally linear knob extending in both directions away from a center pivot. Valve body 333 has an underside opening 343 indicated by an arrow, and the handle 341 is connected to the internals of the positive feed diversion air valve 331 by a valve stem 345. Again, it is understood that a positive feed diversion air valve 331 can have 2, 3, or more bosses 337, each of which has an opening into the central part of the positive feed diversion air valve 331 of a given size and shape and that two oppositely oriented bosses 335 and 337 are ideally required to utilize the two way diversion about to be described. Bosses numbering more than two, which are not utilized can simply be plugged off. Also, it is still preferable to limit the turning of the positive feed diversion air valve 331 when installed for use with the system 21 in order to use the position of the handle 341 as an analog visual indicator for the level of operation of the positive feed diversion air valve 331.

Figure 18:
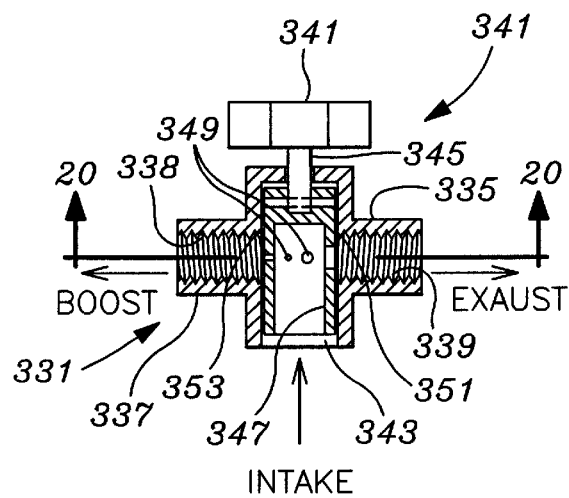
FIG. 18 is a side sectional view taken along line 18—18 of the valve of FIG. 17 and which illustrates the structure and operation thereof.

Referring to FIG. 18, a side sectional view taken along line 18—18 of FIG. 17 indicates the operation of the positive feed diversion air valve 331. The valve main body 333 opening 343 in the bottom of positive feed diversion air valve 331 is the intake opening and situated such that air flow can enter an aligned open end of a cylindrical valve element 347 before being permitted to flow through the bosses 335 or 337. Note that the inside of cylindrical valve element 347 contains a series of small bores 349 which are shown as being roughly vertically centered in the threaded bores 338 and 339. As will be seen, the small bores 349 are distributed about the radius of the cylindrical valve element 347 and extend through the walls thereof, but do not follow a sequential increasing pattern as was seen for vacuum shunt vacuum shunt valve 301. At the innermost end of bosss 337 and 335, bores 338 and 339 present a window openings 351, and 353, respectively. Window openings 351 and 353 expose opposite sides of the cylindrical valve element 347 to flow through respective bosses 337 and 335. In this case, the cylindrical valve element 347 will be used throughout virtually all of its peripheral extent. Again, window openings 351 and 353 are used because it is the view window of the external surface of the cylindrical valve element 347 which is important rather than the overall diameter of the bosses 337 and 335.

However, the linearity achieved in positive feed diversion air valve 331 is not from a position of no flow through the valve to maximum flow, but of 0% diversion to boss 335 and 100% diversion to boss 337 at one end of the operating range and transitioning to a 0% diversion to boss 337 and 100% diversion to boss 335 at the other end of the operating range. Between these two conditions, a linear transition must be made which will preferably not restrict air flow through the positive feed diversion air valve 331. Also, mid-way Between these two conditions, flow is expected to be equally divided between the bosses 337 and 335.

As has been discussed with respect to foot pedal control 51, it is desireable to enable the compression side of the vacuum pump/compressor 141 to have a free flowing condition until the air pressure is needed for boost. Blocking the air supply impedes the use of engine power of the vacuum pump/compressor 141 to exert vacuum. So, much as the foot pedal control 51 invoked a normal condition free venting interrupted by blocking of the venting and pressured power boost from the pressure due to blocking the venting, the same can be done with a valve, in this case positive feed diversion air valve 331.

Figure 19:
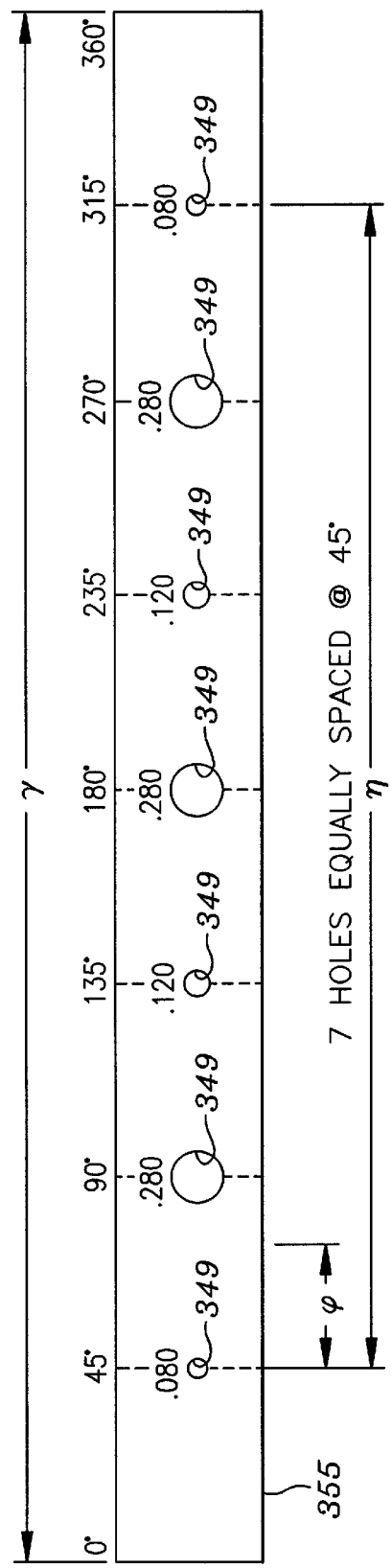
FIG. 19 is a linearized representation of the location of various sized and placed flow apertures on the cylinder element of the valve of FIGS. 17 and 18.

The cylindrical valve element 347 uses almost the total periphery of its surfaces, but an examination of the layout of the small bores 349 in FIG. 19 shows that they do not follow an even stepped value, even over only a 180° length of a linear representation 355. Again, the motion of the cylindrical valve element 347 and the placement of the small bores 347 to create an ever changing multiple combination or "mix" of number and size of small bores 347 which pass across the window openings 351 and 353. Since the end point of the operating continuum will start at 100% flow into one of the bosses 335 and 337 and 0% flow in the other, a first one of the small bores 347 approachs the edge of the window opening 353 (assuming it to be the non flowing side) as the largest one of the small bores 347 begins to move behind the edge of the window opening 351 and have its flow begin to be restricted.

Again, because fluid flow, such as air is very non-linear, a valve opening profile which is percentage proportional to the area available for flow simply will not yield the linearity needed, it is ineffective. Further, since the flow is through two openings, which are oppositely oriented, the geometry of interest involves not only which small bores enter and leave one of the window opening 353 and 351, but also the other one of the window openings 353 and 361 simultaneously. However, since the object is a smooth transition of flow from one side to the other it should be kept in mind that a change in flow area, even on one side alone, affects the percentage split between the two bosses 337 and 335.

The inventive use of a series of well spaced small bores 349, and which are spaced to frame in and frame out of the window openings 351 and 353 as the valve handle 341 is turned will yield a linearization of the relative flows between the bosses 335 and 337, and which is proportional to the angular displacement of the valve handle 341 and stem 345. This enables the physical position of the valve handle 341 to be used as an analog flow indicator to exactly control the magnitude of the air boost.

This enables the operator to have better absolute and reproducable control over the flow of boost air, and to verify the magnitude of the boost through visually checking the position of the valve handle 341. This advance in the valve art is particularly significant for the linearization of needed air, but without blocking the air flow. As with vacuum shunt valve 301, positive feed diversion air valve 331 is provided with a stop to insure that the displacement can occur over a 180° range only, but in this case, since almost 360° of the cylindrical valve element 347 is utilized, the 180° range limitation is functionally necessary. This is best seen in FIG. 19, which illustrates a linear illustration of the placement of the small bores 349 on the cylindrical valve element 347, and is referred to as linear illustration 355. The parameters of this drawing are by way of example only and again depend heavily upon the geometry of the cylindrical valve element 347, including its diameter, height, and the area of the window openings 351 and 353. In this case, the window opening 351 and 351 are again based upon a 0.355 inch diameter internal diameter against the cylindrical valve element 347 to each form a saddle window. The cylindrical valve element 347 is about 0.75 inches in diameter.

It can be seen that the small bores 349 roughly occupy the overall length of the linear representation 355 which is shown as γ, which also corresponds roughly to the 360° operating range of the linear representation 355. The small bores 349 are fairly equally spaced at about 45° each, with there being two of the small bores 349 appearing in each of the window openings 351, 353 at any given time. The miniature bores sequentially occur across the linear representation 355 and have sequential diameters of 0.080, 0.280, 0.120, 0.280, 0.120, 0.280, & 0.080 inches in diameter. The center to center spacing of the first and last small bores 349 is shown as being η, with hole spacing of about 45°. There are seven small bores 349, but there is no small bore 349 at the 0° location.

Using an object of a length of the 180° length of the linear representation 355 and considering one end as representative of one of the window openings 351 and the other end representative of the other of the window openings 353, sliding such object across the linear representation 355 will give an idea of the pairs of small bores 349 which appear simultaneously in their respective window openings 351 and 353. Beginning at the left, and assuming that 0° is associated with the window opening 351, the window opening 351 has no available small bore 349, while the largest window opening 353 at 180° is associated with the window opening 353. Moving to the right, window opening 351 becomes associated with 0.080 inch small bore 349 as window opening 351 becomes dis-associated with the 0.280 inch diameter small bore 349 and becomes associated with the 0.120 inch diameter small bore 349. As the window opening 351 becomes dis-associated with the 0.080 inch small bore 349 and associated with 0.280 inch small bore 349, the window opening 351 becomes dis-associated with the 0.120 inch small bore 349 and associated with the 0.280 inch diameter small bore 349 at the 180° mark, and so on.

At the end of the angular travel of the cylindrical valve element 347, the flow through the window opening 351 becomes fully open while flow through the window opening 353 becomes fully closed.

Figure 21:
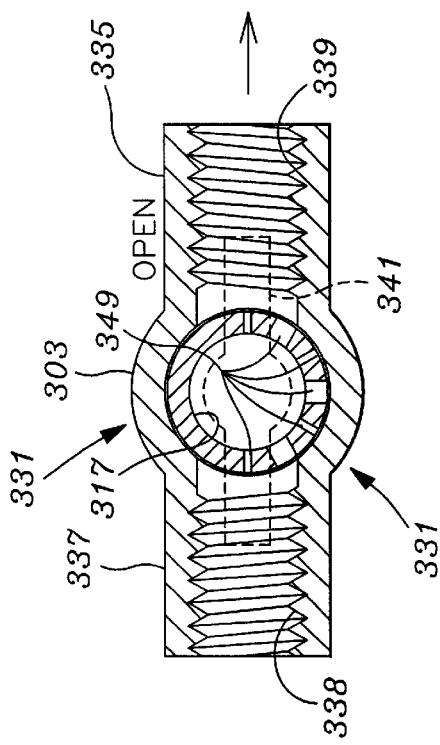
FIG. 21 is a view similar to that of FIG. 20 and showing angular displacement of the cylindrical valve element of the valve of FIGS. 17–20 as it is operated.
Figure 20:
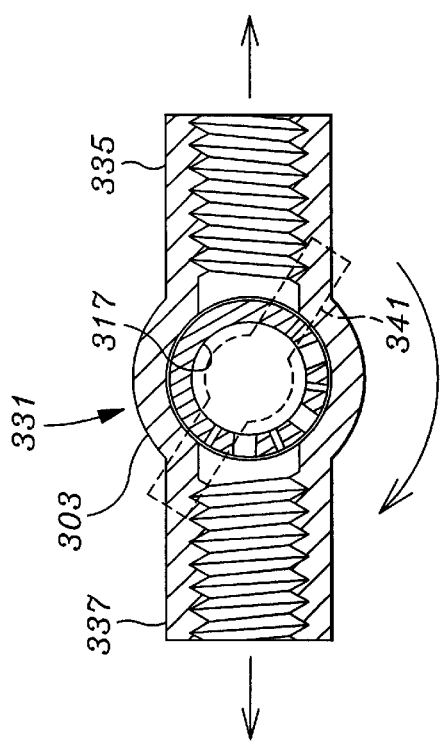
FIG. 20 is a view taken along line 20—20 of FIG. 19 and illustrating the position of the cylindrical valve element of the valve of FIGS. 17–19 as it is operated.

FIG. 20 is a sectional view of the positive feed diversion air valve 331 taken along line 20—20 of FIG. 18 and which illustrates the position of the small bores 349 when the valve is in a position to pass 100% of the flow through boss 335. FIG. 21 illustrates initial movement of the cylindrical valve element 347 beginning the shift of air flow into boss 337, and which in accord with the angle of the valve handle 341 is expected to be about 75% through boss 335 and 25% through boss 337.

Figure 22:
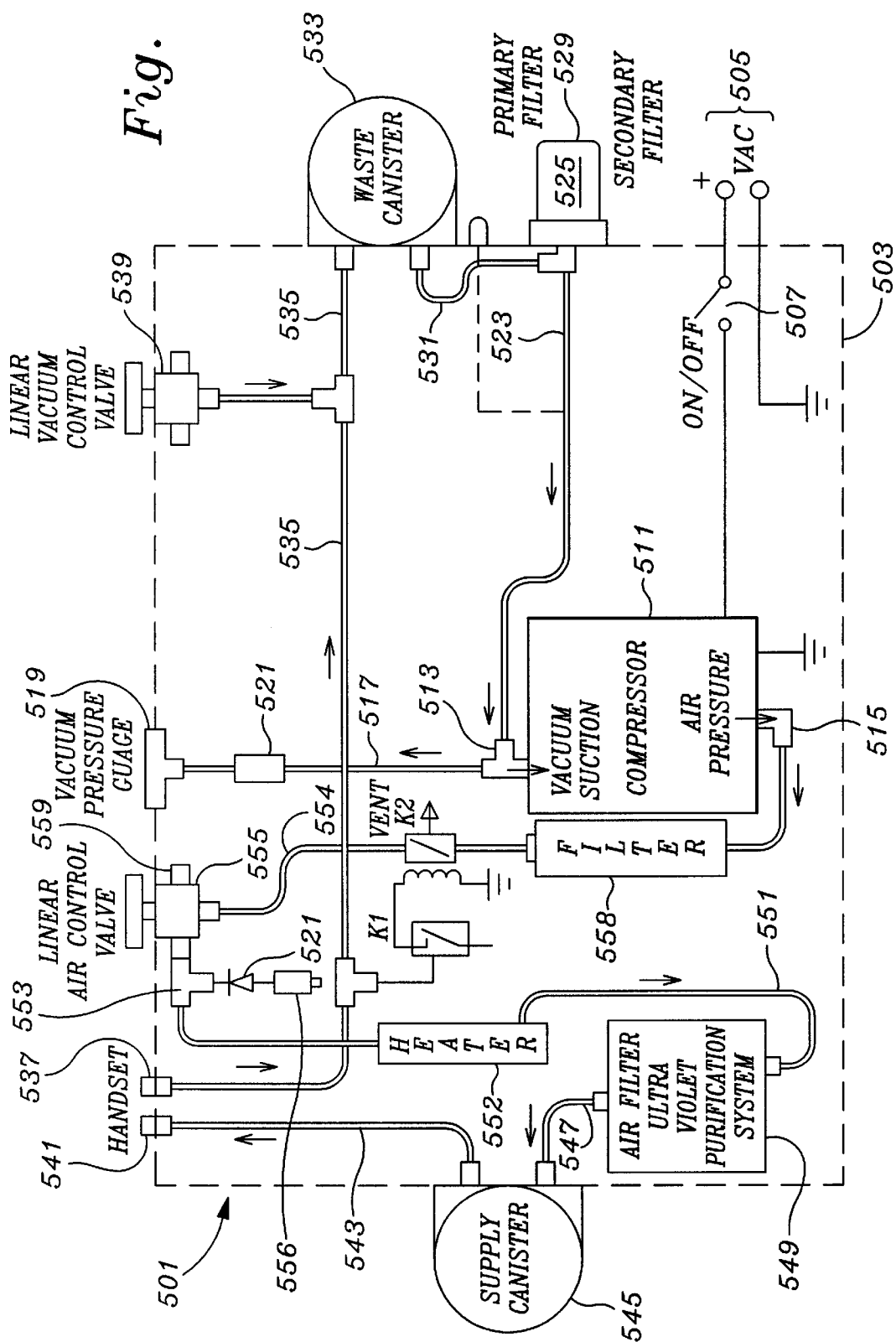
FIG. 22 is an overall schematic of a second embodiment of the system of the invention.

The system 501 initially shown in FIG. 22 is especially needed where use is to be accomplished by technical personnel doing the same types of abrading jobs, and where management of the system is to be foolproof, where no amount of reasonable tampering will violate the protocol to use fresh supply media only and to isolate the waste media as much as possible.

System 501 is a Direct Linear Vacuum/Air Control System utilizing two custom developed valves, one for air pressure and one for vacuum control (these valves are patent applied for in this package). These valves provide a positive linear control from "no air/vacuum", a setting of one (1) on the control knob, to "maximum air/vacuum", a setting of five (5) on the control knob, with a full 180 degree movement from minimum to maximum of the control knob providing smooth positive and linear flow control.

Referring to FIG. 22, and generally speaking, a system 501 utilizes a custom vacuum operated, electric actuated, air flow control valve to block all air boost operations at vacuum levels under 10 inches of mercury. This three way soleniod operated valve will not actuate until the handset tool 75 has the opening 103 occluded (closed) by material to be abraded and a vacuum of over 10 inches of mercury developed at the vacuum gating valve. If the vacuum is not developed the air boost system will not operate under any conditions. If the system is in use and the handset is occluded and vacuum is over 10 inches of mercury and air boost is on and the operator removes the handset tool 75 from the material being abraded, vacuum is immediately lost, the air boost system closes by the soleniod and no media escapes through the handset tool 75 opening 103 because all media flow is inhibited.

System 501 utilizes an advanced design in the supply of abrasive media and the collection and control of waste media and abraded material described in FIGS. 7–11. Disposable supply media and waste cannisters are provided in matched pairs and both caintainers are replaced simultaneously. The supply system design allows for supply media to be provided in sealed media containers and installed onto the system by the operator by a 180 degree rotation lock. The waste media container is a self contained unit with a 360 degree lock, backflow stop (waste goes in but cannot get back out), a filter system and a outside metal jacket. Disposal of the empty media container and the full waste cannister is controlled by the owner/operator.

The system 501 of FIG. 22, is especially useful in the cosmetology and medical field is shown as system 501 and is oriented similarly to the system 21 of FIG. 6. A housing 503 will be of adequate size to support the components therein, and at least two housing embodiments will be shown. Electrical power is provided to the system 501 with a regular wall outlet 505. An on/off switch 507 controls power availability into the housing 503, A vacuum/compressor 511 is seen. Vacuum/compressor 511 has a one way air flow action which sucks into at least one port 513 and produces a pressurized output through at least one port 515. Each half stroke of the piston produces a vacuum at port 143, while the next half stroke of the piston within the vacuum/compressor 511 produces a pressurized output at port 515.

The vacuum side of the system 501 includes port 513, line 517 connected to vacuum guage 519 through a restrictive orifice 521. A vacuum line 523 connects to a secondary filter 525, typically mounted for visual inspection on the outside of the housing 503, and which is connected through a connector tube 531 to waste canister 533 which holds primary filter 233 seen in FIG. 8. Waste canister 533 is preferably as seen in FIGS. 7–9. From waste canister 533, and after providing flow through filter 233, the flow continues through a line 535 which extends to a fitting 537 which may be color coded black to help prevent unintended reversal of the hoses 77 and 79 seen in the earlier Figures. A "T" shaped fitting leads to a linear vacuum control valve 539 which can shunt atmospheric air into the vacuum produced in the line 535. Vacuum controlvalve 539 can be of many different designs, but the design of vacuum shunt valve 301 of FIGS. 12–16 will preferably be used for the vacuum control valve 539. Note that in this configuration, the shunt is introduced into the general vacuum sequence of lines and filters immediately before the port 537 on the way to the manual contact tool 75. (In FIG. 6, the valve 149 shunted air virtually directly into the vacuum pump/compressor 141, thereby using the waste canister as a vacuum buffer.

A "T" connection is used to enable a vacuum sensor switch K1 to be put into fluid communication with the vacuum in the line 535 immediately before the port 537. Once the vacuum in the line 535 is high enough, say above 10 inches of mercury, a relay scheme operates a shunt valve K2 which makes air pressure available to the supply side of the system, from the port 515. When the vacuum in the line 535 is below 10 inches of mercury, the pressure available to a solenoid valve K2 from the port 515 is simply shunted to atmosphere within the housing 503. Diversion of flow from the vacuum pump/compressor 511 is to both (1) prevent air from flowing through to begin ejecting abraisive material which would inadvertently be emitted, and (2) avoid loading the vacuum pump/air compressor 511 which would render the vacuum too low to be of any use, by throttling the system.

Continuing with the vacuum portion of the system 501, a vacuum is presented to port 537 into the vacuum side of the manual contact tool 75. If opening 103 of the cap 101 is occluded by pressing the manual contact tool 75 over the area to be abraded, the vacuum will be presented to port 541 to enable a mixture of abraisive material and air to be drawn through a line 543 from a supply canister 545. System 501, like the system 21, can operate purely in vacuum mode, and pull ambient air from the surroundings of the housing 503 and then through the system 501. However, during the pressure boost, the pressurized air was air from the vacuum pump/compressor which was previously drawn through the vacuum/compressor 511 as the exhaust of the vacuum system, with air coming into port 513. Even though the waste canister 533, primary filter 223 and secondary filter 525 are expected to completely, although mechanically, remove all abraisive material and abraded material from the vacuum inlet line 523, the very remote possibility exists that extremely tiny amounts of contaminated material might be able to get through. The primary filter 223 and secondary filter 525 are expected to be about five micron size, but can be different sizes, for example, gradually smaller in filtration size, but correspondingly larger in surface area to prevent undue pressure drop.

One optional device, in order to make absolutely certain that no contaminated material passes through vacuum/compressor 511 to re-enter the system 501, even through regular operation, filter failure or rupture and the like, an input line 547 into the supply canister 545 is made to first pass through the 0.7 micron filter 558 long before it reaches the ultraviolet purification system 549. Typically the ultraviolet purification system 549 will provide an expanded area filter system illuminated by an ultraviolet light, and with sufficient flow residence time so that if a contaminated particle was introduced, it would be exposed to ultraviolet radiation that would kill it.

The input to the ultraviolet purification system 549 is fed by a line 551, which may also optionally be connected through a heater 552 which may preferably be a ceramic heater. The heater is placed so that heat added to the air will work in conjunction with the ultraviolet purification system 549, increasing its effectiveness by providing a higher temperature process stream for ultraviolet irradiation. In addition, any heat in the input line 547 will have an opportunity to be absorbed by the media in the supply canister 545. Further, an additional heat exchanger can be added as a part of inlet line 547, or as a part of line 543. Preferably, either of the lines 547 or 543 will take a serpentine path along with perhaps both an attachment to a metal wall of housing 503 and heat fin on the lines 547 or 543 and possibliy on the outside of a wall of the housing 503.

Line 552 is then connected through a "T" fitting 553 which is used for mounting a relief valve 554 to a control valve 555, which is preferably subject to linear operation. To insure that only completely filtered air enters the system 501 through the relief valve 554, a 0.07 micron air filter 556 is attached at the end of the relief valve 554 to insure that entering air is very well filtered.

Control valve 555 is preferably configured as positive feed diversion air valve 331 as seen in FIGS. 17–21, but can be any configuration. The valve 555 has one input connected to a line 557 which connects back to the port 515 through a filter 558, which preferably has a filtration size of about 0.7 micron. The filter 558 limits the re-introduction into system 501 of any contaminated particles which may have made it through the filtration provided prior to the vacuum suction of the vacuum pump/compressor 511. The valve 555 has a second port 559 which is an air dump, preferably fritted or filtered to disperse air going into or out of the valve 555.

However, it is desired that control valve 555 operate between a condition of full air purge through the second port 559, with the input air being diverted over to line 552 Again, if the control valve 555 is set to completely divert air 100% through the second port 559, and closed to the line 552, the relief valve 553 can open to admit air into the line 551 for vacuum level operation.

The valve 555 is arranged so that it can open air into the line 552 during vacuum operation and such that it can control the pressurized air supplied through line 557, either by diverting through second port 559, or by controlling the magnitude of air which is able to reach the line 551. But before the linear air control valve 555 can operate on any inlet air, the shunt valve K2 must be in an operational position to pressurize line 557 by being set not to divert air to the exhaust port of shunt valve K2. Operation of K2 should preferably require a vacuum of 10 inches of mercury at the relay K1.

The system 501 can be constructed without the air boost capability by simply allowing port 515 of the vacuum pump/compressor 511 to simply vent to the surrounding atmosphere, and eliminating shunt valve K2, valve 555, heater 552, and ultraviolet purification system 549. In addition, "T" mounted relief valve 553 would be placed in line 547 with filter 558 and optionally a muffler. The result will be a system which still has vacuum only operation, but which still has the supply and waste cannister configuration seen in FIGS. 7–11.

Figure 23:
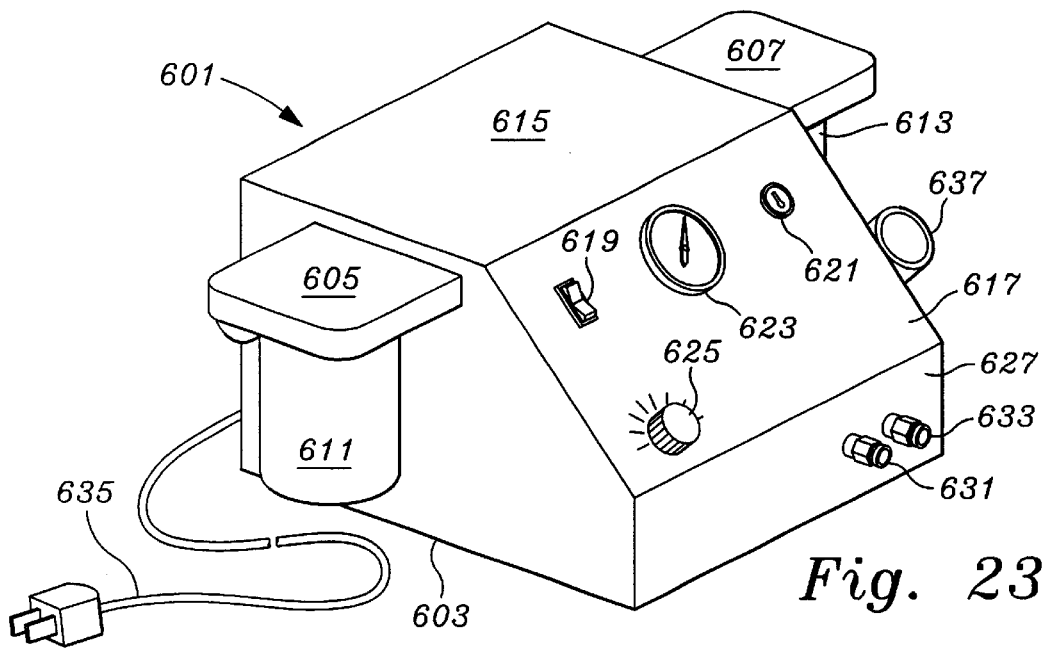
FIG. 23 is a perspective view of one configuration of a housing especially suited for housing the second embodiment of the invention configured for safe use in the cosmetology field and configured for vacuum-only operation.

Referring to FIG. 23, a vacuum only system 601 is seen which is intended primarily for the cosmetology market. The vacuum only operation is believed to be more suitable for non-medical personnel. The system 601 has a main housing 603, and a pair of oppositely located side supports 605 and 607. Side support 605 supports a waste canister 611 while side support 607 supports a supply container 613.

The main housing 603 includes a top plate 615 and angled front plate 617 which contain the operating components of the system 601. Front plate 617 supports an ON/OFF rocker switch 619 which is used to turn the system 601 on and off, but only providing the lockout key is inserted into the lockout safety switch 621 and that the lockout safety switch 621 is closed. At the center of the front plate 617 is a vacuum pressure gauge 623. To one side of the vacuum pressure guage 623 a valve handle 625 is surrounded by a series of numerical designations on the front plate 617 which give a visual indication of the displacement of the valve handle 625 for operation of an internal vacuum control valve, preferably vacuum shunt valve 301 of FIGS. 12–16.

Below the slanted flont plate 617 is a front vertical plate 627 which support pair of quick connect fittings 631 and 633 to which are connected hoses 47 and 49 seen in 77 and 79 seen in FIG. 1 and which lead to the manual contact tool 75. Also seen is an electrical power cord 635, and a cylindrical support 637 for supporting the manual contact tool 75 when it is not in use.

Figure 24:
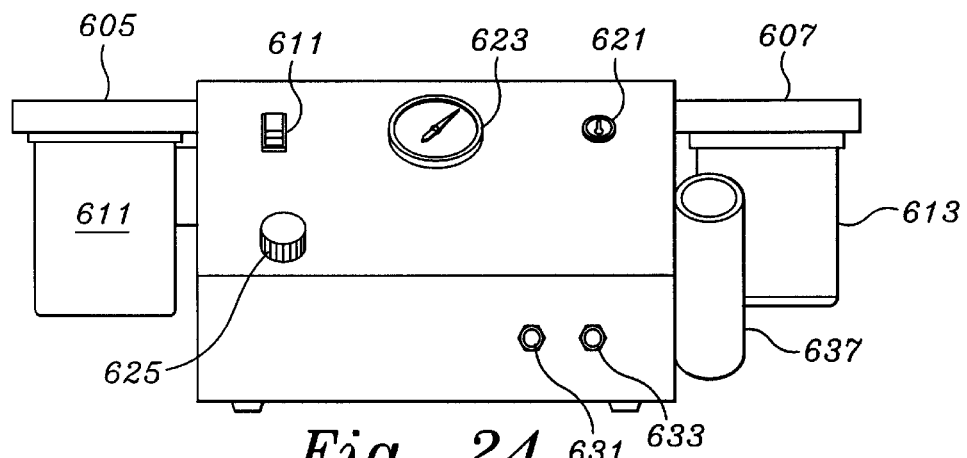
FIG. 24 is a front view of the housing of FIG. 23.
Figure 25:
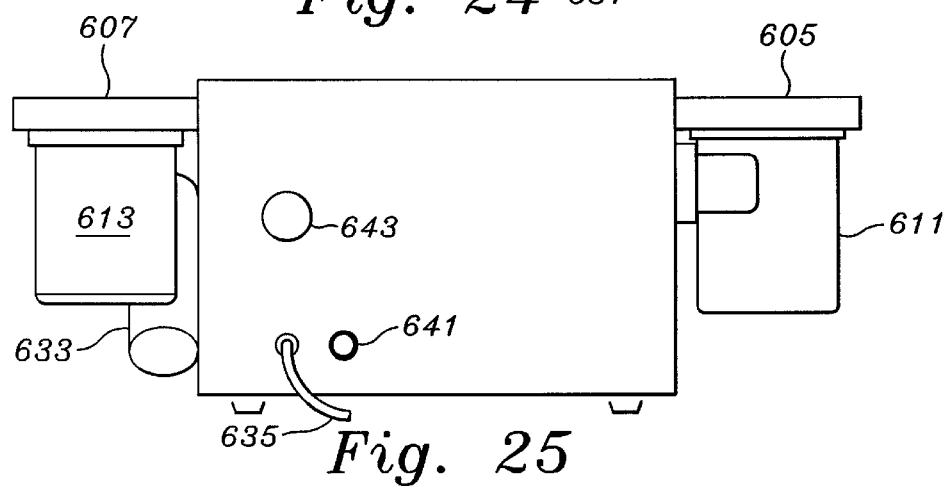
FIG. 25 is a rear view of the housing of FIGS. 23 and 24.

Referring to FIG. 24, a front view of the system 601 is seen. Referring to FIG. 25 a rear view shows a fuse 641, and also a glass cover 643 for both operation of and visual inspection of the secondary filter 525 seen in FIG. 22. The cover 643 is typically threadably removable to change the filter element contained inside. Both the supply canister 613 and the waste canister 611, in accord with the teaching of FIGS. 7–11, are preferably threadably removable.

Figure 26:
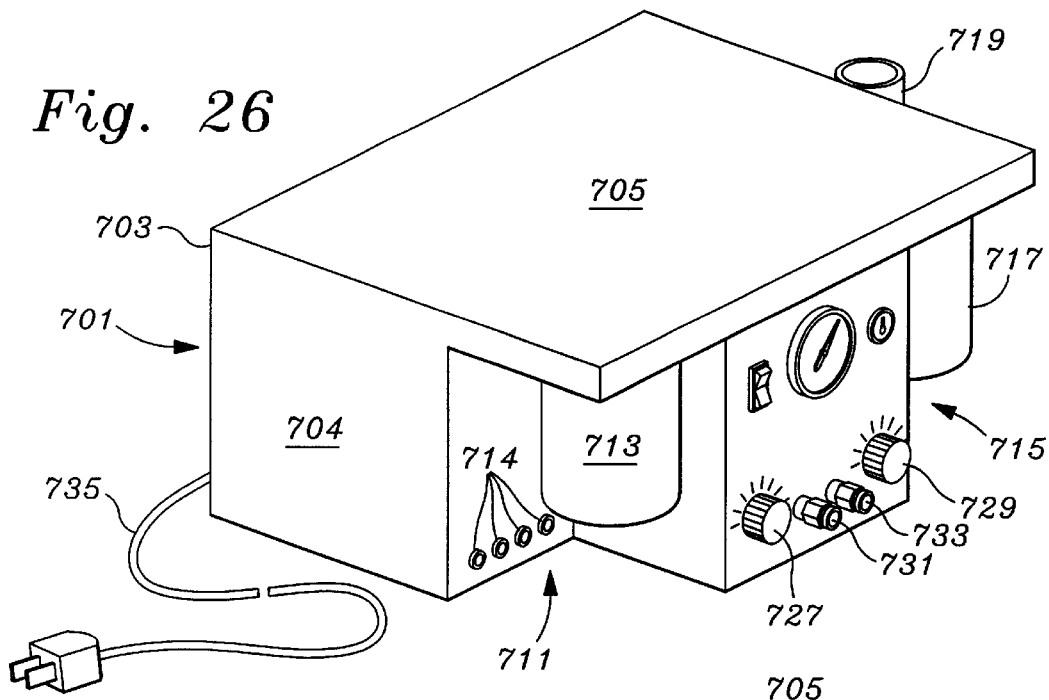
FIG. 26 is a perspective view one configuration of a housing for the second embodiment of the invention with vacuum and boost capability, configured for safe use in the medical field and configured for vacuum-only operation.

Referring to FIG. 26, a vacuum and boost system 701 is seen which is intended primarily for the medical market. The increased power from combined boost and vacuum operation is believed to be more suitable for well trained medical professionals. The system 701 has a main housing 703, and an integrated top cover 705 and a front vertical panel 707. A side 709 and front panel 707 are abbreviated due to a rectangular accommodation space 711 for accommodating the vertical support of a waste canister 713. Within the accommodation space 711, and just underneath waste canister 713, a series of four optical indicators 714 are seen. These optical indicators 714 are optional and may be connected to any of a number of internal structures and systems for showing a fault. Preferably the optical indicators 714 each correspond to a separate bulb illuminating an ultraviolet system (seen in FIGS. 29–31). Ideally, and for long life and reliability the optical indicators 714 will be of the fiber optic type and will indicate an ultraviolet bulb fault directly, through transmission of light along the fiber optic cable.

Another accommodation space 715 accommodates the vertical support of a supply canister 717. At the far side of the main housing 703 is a cylindrical support 719 for supporting the manual contact tool 75 when it is not in use.

Front vertical panel 707 the operating components of the system 701. Front panel 707 supports an ON/OFF rocker switch 721 which is used to turn the system 701 on and off, but only providing the lockout key is inserted into the lockout safety switch 723 and that the lockout safety switch 723 is closed. At the center of the front plate 707 is a pressure gauge 725. To one side and below of the pressure guage 725 a valve handle 727 is surrounded by a series of numerical designations on the front plate 717 which give a visual indication of the displacement of the valve handle 3155 for operation of an internal vacuum control valve, preferably vacuum shunt valve 301 of FIGS. 12–16. To the other side and below of the pressure guage 725 a valve handle 729 is surrounded by a series of numerical designations on the front plate 717 which give a visual indication of the displacement of the valve handle 315 for operation of an internal pressure boost control valve, preferably valve 351 of FIGS. 17–21.

Also supported by the panel 707 is a pair of quick connect fittings 731 and 733 to which are connected hoses 47 and 49 seen in 77 and 79 seen in FIG. 1 and which lead to the manual contact tool 75. Also seen is an electrical power cord 735.

Figure 27:
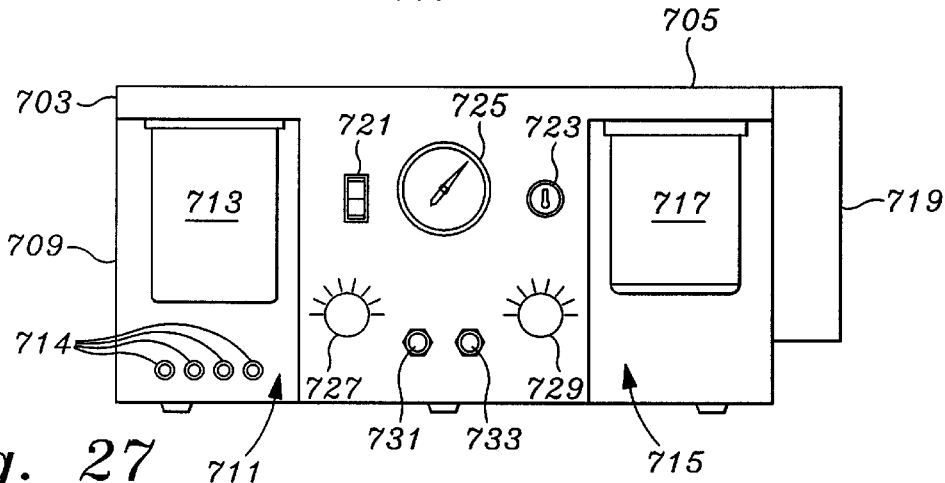
FIG. 27 is a front view of the housing of FIG. 26.
Figure 28:
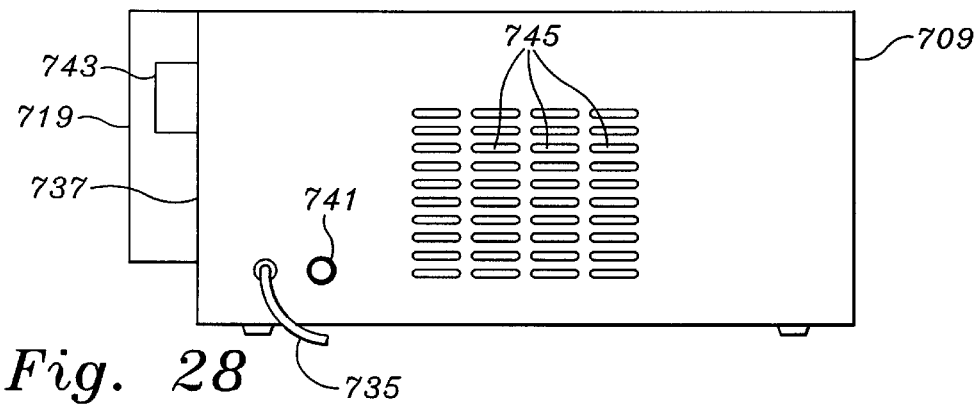
FIG. 28 is a rear view of the housing of FIGS. 26 and 27.

Referring to FIG. 27, a front view of the system 701 is seen, and indicating a side wall 737. Referring to FIG. 28 a rear view shows a fuse 741, and also a glass cover 743 extending out of the side of the system 701 for both operation of and visual inspection of the secondary filter 525 seen in FIG. 22. The cover 743 is typically threadably removable to change the filter element contained inside. Both the supply canister 713 and the waste canister 717, in accord with the teaching of FIGS. 7–11, are preferably threadably removable. Also seen is a ventilation opening 745.

The system 501, both with and without embodiment into the physical realization of the systems 601 and 701, and which will be discussed collectively as systems 501, 601 and 701 gives a number of advantages in addition to the advantages had with the system 21. The systems 501, 601 and 701 eliminates the operator handling of used media with a sealed self contained disposable waste container 213, as seen in FIGS. 7–9. Systems 501, 601 and 701 facilitate the utilization of the new linear vacuum vacuum shunt valve 301 of FIGS. 12–16 and air boost valves 331 of FIGS. 17–21 to give the operator a much finer range of adjustment of the abrasion effectiveness and comfort to the patient. In addition, on start up of the systems 501, 601 and 701, the visual relationship between the position of the valves 301 and 331 enable the operator to preset the machinery before use, and eliminate the "hunt" for the proper operating conditions by trial and error, and at patient expense.

The supply of new media is bottled in its own container that is now multiply sealable before shipment and receipt by the user. Many seal structures can be employed to insure integrity and purity of the supplied abraisive product. The supply can then remain sealed until it is uncapped to screw onto a support structure of a machine embodying the systems 501, 601 and 701.

The capacity of the supply canister 267 and waste collection canister 213 of FIGS. 7–11 cut the time lost for having an operator handle the abraisive material, such as for emptying and refilling the machine of systems 501, 601 and 701, by at least 90%. The vacuum safety switch and solenoid valve shown in FIG. 22 as vacuum sensor switch K1/solenoid valve K2 that sets a vacuum pre-condition for control of the the air boost, eliminates the possibility of inadvertently blowing abraisive media when the manual contact tool 75 is in not in position and when at least ten inches of mercury vacuum is not present at the end of the manual contact tool 75.

The use of vacuum sensor switch K1/solenoid valve K2 as a shunt valve configuration, acts as one possible mechanism for elimination of foot pedal control 51 for a freer mode of operation, or if it is desired, a greater degree of control of the abrasive media can be hand if the optional foot pedal control 51 of FIG. 6 is used. As the operator takes a break from manipulation of the manual contact tool 75 by breaking contact of the opening 103 from the skin surface, the shunt valve K2 automatically diverts the air supply before the air boost can even reach the linear air control valve 555. This frees the operators to only concern themselves with the manual contact tool 75, and its relationship with the area to be abraded. Elimination of a foot control 51 also frees the operators to move around and situate themselves with regard to the work area. If a foot pedal control 51 is desired, it can be provided, especially if the operator is in surroundings where the operator will be constantly positioned, or where even greater control is required, although it is expected that this will more likely occur during non-medical utilization of system 21 or the like.

The disposable cap 101 on the manual contact tool 75 that is replaced for each patient insures sanitary conditions of the treatment. The manual contact tool 75 is easier to hold and is balanced for optimum comfort of the operator. The provision of a large vacuum gauge is easier for the operator to see in order to make accurate adjustments.

Figure 29:
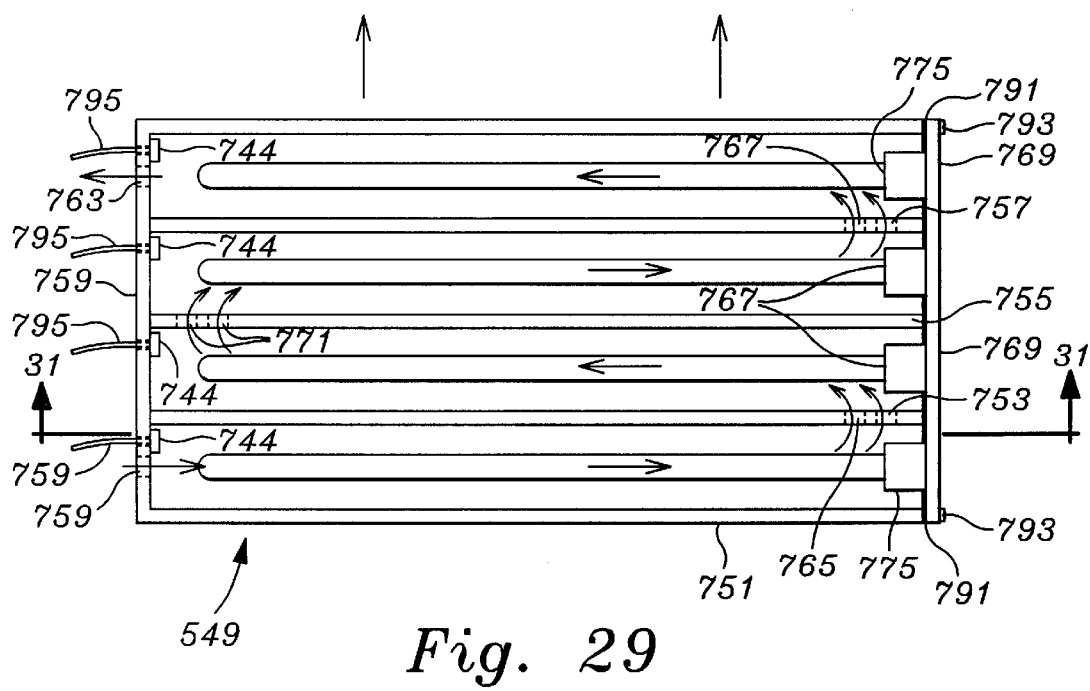
FIG. 29 is a plan view of a housing of an ultraviolet purification system with internal baffles to create a serpentine flow in the presence of ultraviolet light.

Referring to FIG. 29, one embodiment of the ultraviolet purification system 549 is seen. A view looking downward on the ultraviolet purification system 549 illustrates a housing 751 which is rectangular in shape and having a series of three internal baffles 753, 755, & 757. One wall 759 has an inlet aperture 761 spaced apart from an exit aperture 763. Baffles 753 and 757 have apertures 765 and 767 nearer an end wall 769. Baffle 755 has a set of apertures 771 nearer the wall 759. As can be seen, the baffles 753, 755, & 757 in combination with the apertures 765, 767 and 771 and the inlet aperture 761 and exit aperture 763 create a serpentine flow space for air entering the ultraviolet purification system 549.

Removable wall 769 supports a series of identical electrical sockets 775. An ultraviolet light 777 is shown in one of the sockets 775 and is seen to occupy the bulk of the length of the ultraviolet purification system 549. The purpose of the structure of the ultraviolet purification system 549 is to give air flowing therethrough adequate exposure to the lights 777 and contact with the ultraviolet electromagnetic light rays from the ultraviolet lights 777. The dimensions of the ultraviolet purification system 549 housing is preferably about eight inches by eight inches by six inches, with the eight inch dimensions shown in FIG. 29. The bulbs may have a wattage rating of from about 16 to about 20 watts of power.

Figure 30:
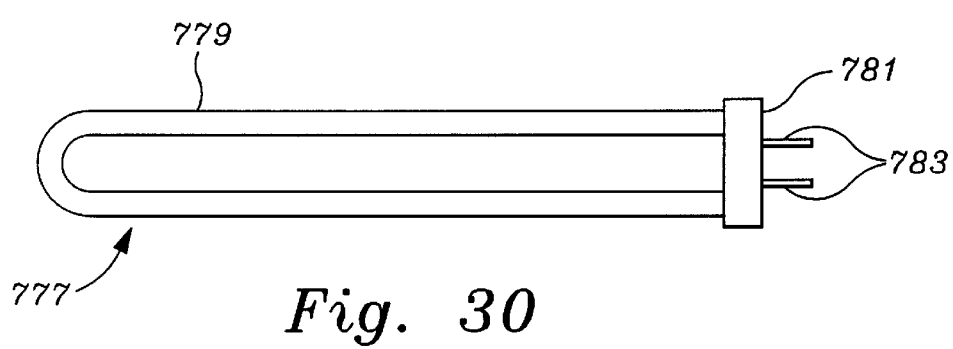
FIG. 30 is a side view of an ultraviolet bulb shown in FIG. 29.

Referring to FIG. 30, a side view of a bulb 777 has a curved fluorescent type tube 779 and is supported by a base 781. The base 781 has a pair of electrical prongs 783 for insertion into mating plugs in the electrical sockets 775. Changing of the bulbs 777 merely involves opening the eight inch by six inch wall on the ultraviolet purification system 549, and unplugging burned out bulbs 777 and replacing with new bulbs 777. Also as seen in FIG. 29 is a seal 791 and a set of screws or bolts 793 which hold the removable wall 769 in place. At the left side of the purification system 549 a series of fiber optic sensors 794 are seen, each having a fiber optic cable 795 extending away from purification system 549. The fiber optic cables 795 send light back to the four optical indicators 714 seen in FIGS. 26 and 27. The structures of the purification system 549 are shown with an upper wall removed for clarity.

Figure 31:
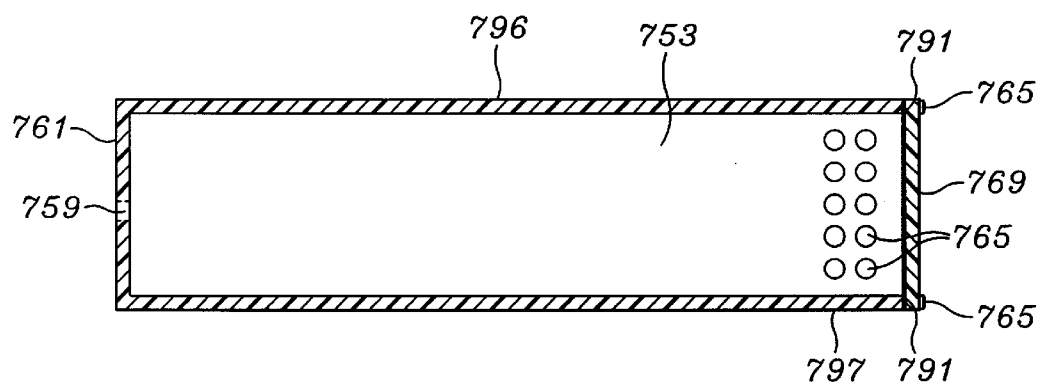
FIG. 31 is a side view of the housing of an ultraviolet purification system with internal baffles to create a serpentine flow in the presence of ultraviolet light.

Referring to FIG. 31, and also as seen in FIG. 29 is a seal 791 and a set of screws or bolts 793 which hold the end wall 769 in place. The side sectional view in FIG. 31, seen with the top wall 796 in place, better illustrates the attachment of the removable wall 769. The apertures 765 are seen for creating the serpentine air flow pattern. FIG. 31 is a sectional view taken along line 31—31, of the ultraviolet purification system 549 which is expected to be made of silver anodized metal for maximum reflectivity of the germicidal ultraviolet wavelength emissions of the ultraviolet light 777 within the system 549. Also seen in FIG. 31 is a bottom wall 797. It is understood that the ultraviolet purification system 549 can be built in any dimension, the only requirement is that an adequate number of bulbs 777 and of adequate power rating are used along with a ultraviolet purification system 549 of sufficient size that the air flow has sufficient residence time for adequate irradiation.

Generally, the external system 705 corresponds to the system 501 in FIG. 22, but since so many variations on the system 501 are possible, and within the physical realization of FIGS. 26–28 it is essentially a physical realization system 701 and may have a wide variety of structures, which have a relationship similar to that shown in FIG. 22. Similarly, the external system 601 corresponds to the system having less than the full capability of system 501 of FIG. 22, but again having the possibility of a large number of variations. Since the system 501 shows a large number of the components which are possible, and which would be accommodated by the system 701 of FIGS. 26–28, a vacuum only schematic system will be shown which would be accommodated by the system 601.

Figure 32:
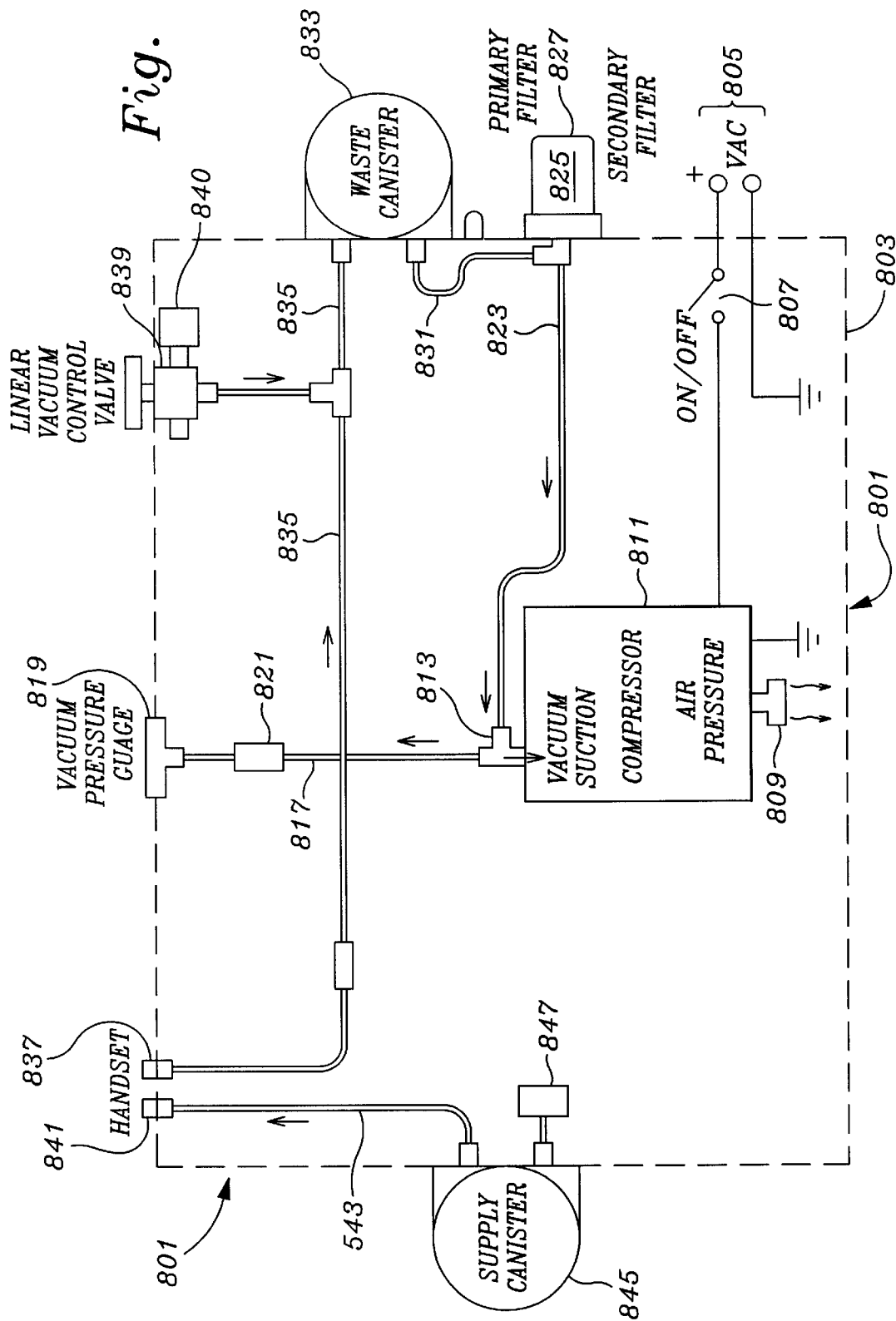
FIG. 32 is a view of a vacuum only system as a third embodiment which incorporates many advantages of the full system seen in FIG. 22, but without the air boost capability, and which is compatible with the housing systems of FIGS. 23–25.

Referring to FIG. 32, a schematic view of a vacuum only system 801 is shown. System 801 also utilizes the advanced design in the supply of abrasive media and the collection and control of waste media and abraded material described in FIGS. 7–11. The system 801 of FIG. 32, is especially useful in the cosmetology and medical field is shown. A housing 803 will be of adequate size to support the components therein, and the housing of system 701 is preferred. Electrical power is provided to the system 801 with a regular wall outlet 805. An on/off switch 807 controls power availability into the housing 803. However, a diffuser 809 is seen in a vacuum/compressor 811 to make sure that air which is ejected as a result of the vacuum operation escapes freely into the surrounding area. As explained, to allow pressure to build in the pressure side of the vacuum/compressor 811 robs it of the power which is otherwise used to create vacuum. The vacuum side of the vacuum/compressor 811 has a one way air flow action which sucks into at least one port 813, into a line 817 connected to vacuum gauge 819 through a restrictive orifice 821. A vacuum line 823 connects to a secondary filter 825, typically mounted for visual inspection on the outside of the housing 803 with a clear housing 827. The secondary filter 825 is connected through a connector tube 831 to waste canister 833 which holds a primary filter 233 seen in FIG. 8. From waste canister 833, after providing flow through filter 233, the flow continues through a line 835 which extends to a fitting 837 for connection to the manual contact tool 75. A "T" shaped fitting leads to a linear vacuum control valve 839 which can shunt atmospheric air into the vacuum produced in the line 835, and may have an inlet filter-difusser 840. Again, vacuum control valve 839 is preferably the vacuum shunt valve 301 of FIGS. 12–16.

The other connection to the manual contact tool 75 is through a fitting 841, which then communicates through a line 843 from a supply canister 845. Supply canister 845 has a filter-diffuser fitting 847 to draw clean surrounding air into the supply canister 845 where it is used to fluidize and draw a supply of air and abrasive material toward the fitting 841. Since the inlet air is clean air, ultraviolet treatment and heat treatment is not expected to be needed and filter-diffuser fitting 847 can have a small particulate filtering size, and at least as small as inlet filter-difusser 840. The inlet filter-diffusers 840 is meant to prevent particulates from entering the supply canister 845, and whether it is considered to be a diffuser or filter will depend upon the size of particulates which it admits.

While the present invention has been described in terms of an abrasion system and hand-held instrumentation therefor, one skilled in the art will realize that the structure and techniques of the present invention can be applied to many appliances including any appliance where a vacuum or vacuum and pressure boost system are used to impact abrasive material against a surface to be abraded and especially where a sterile operating system is needed.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. An abrasion system comprising:
   a first source of supply of flowing air carrying abrasive particles;
   a first source of collection of flowing air carrying at least one of abrasive particles and abraded material; and
   a manual contact tool having a first end for directing toward an area of material to be abraded; and having an inlet bore opening at a radial center of said first end of said manual contact tool and in fluid communication with said first source of supply of flowing air, said manual contact tool having a plurality of exit openings spaced apart from said inlet bore opening and in fluid communication with said first source of collection of flowing air; and
   a housing cover having a first end having an opening for contact with said material to be abraded and a second end, said opening of said housing cover in alignment with said inlet bore opening, and said second end of said housing cover surrounding said inlet bore opening and said plurality of exit openings.

2. The abrasion system as recited in claim 1 and wherein said plurality of exit openings spaced apart from said inlet bore opening are evenly radially distributed about said inlet bore opening.

3. An abrasion system comprising:
   a first source of supply of flowing air carrying abrasive particles;
   a first source of collection of flowing air carrying at least one of abrasive particles and abraded material; and
   a manual contact tool having a first end for directing toward an area of material to be abraded; and having an inlet bore opening at a radial center of said first end of said manual contact tool and in fluid communication with said first source of supply of flowing air, said manual contact tool having an exit opening spaced apart from said inlet bore opening and in fluid communication with said first source of collection of flowing air; and
   means to disable said first source of supply of flowing air carrying abrasive particles when said first source of collection of flowing air carrying at least one of abrasive particles and abraded material is above a first threshold pressure.

4. An abrasion system comprising:
   a first source of supply of flowing air carrying abrasive particles;
   a first source of collection of flowing air carrying at least one of abrasive particles and abraded material; and
   a manual contact tool having a first end for directing toward an area of material to be abraded; and having an inlet bore opening at a radial center of said first end of said manual contact tool and in fluid communication with said first source of supply of flowing air, said manual contact tool having an exit opening spaced apart from said inlet bore opening and in fluid communication with said first source of collection of flowing air; and
   wherein said manual contact tool includes a plurality of exit openings and an exit collection chamber in fluid communication with said plurality of exit openings and in fluid communication with said first source of collection of flowing air and interposed between said plurality of exit openings and said first source of collection of flowing air.

5. The abrasion system as recited in claim 4 and wherein said first source of supply of flowing air carrying abrasive particles further comprises:
   a supply container; and
   a venturi tube having a first end through which flowing air carrying abrasive particles passes in fluid communication with said inlet bore of said manual contact tool and an inlet orifice along a length of said venturi tube and within said supply container.

6. The abrasion system as recited in claim 5 and wherein said venturi tube also has a second end in ultimate fluid communication with the surrounding air.

7. The abrasion system as recited in claim 6 and wherein said supply container has an entrance air supply opening to a bottom of said supply container to fluidize any abrasive particulates located in said supply container.

8. An abrasive particle delivery and retrieval system comprising:
   a housing;
   a vacuum pump supported by said housing and having a vacuum inlet for creating a source of vacuum power;
   a vacuum control valve in fluid communication with said vacuum inlet for shunting air into said vacuum inlet to control the amount of vacuum transmitted by said vacuum pump, said displacement position of said position selectable valve directly proportional to the flow of said pressurized air vented by said vacuum control valve;
   a vacuum port supported by said housing and in fluid communication with said vacuum inlet of said vacuum pump; and
   a supply container supported by said housing and having a supply port for supplying a flowing air carrying abrasive particles and an air inlet port.

9. The system as recited in claim 8 wherein the displacement position of said vacuum control valve is directly proportional to the flow of air shunted into said vacuum inlet.

10. The system as recited in claim 8 and further comprising a vacuum gauge supported by said housing and in fluid communication with said vacuum inlet of said vacuum pump for displaying the vacuum developed by said vacuum pump.

11. The abrasion system as recited in claim 8 and wherein said supply container further comprises a venturi tube having a first end through which flowing air carrying abrasive particles passes in fluid communication with said supply port, a second end for admitting flowing air into said venturi tube, and an inlet orifice between said first and said second ends of said venturi tube and within said supply container in a position to admit abrasive particles into said venturi tube when said supply container contains an effective amount of abrasive material to feed into said inlet orifice.

12. The abrasion system as recited in claim 11 wherein said venturi tube has a "U" shape and wherein said inlet orifice is located adjacent a lowest extent of said "U" shape.

13. An abrasive particle delivery and retrieval system comprising:
   a housing;
   a vacuum pump supported by said housing and having a vacuum inlet for creating a source of vacuum power;
   a vacuum control valve in fluid communication with said vacuum inlet for shunting air into said vacuum inlet to control the amount of vacuum transmitted by said vacuum pump;
   a vacuum port supported by said housing and in fluid communication with said vacuum inlet of said vacuum pump; and
   a supply container supported by said housing and having a supply port for supplying a flowing air carrying abrasive particles and an air inlet port;
   a waste canister system interposed between said vacuum port and said vacuum inlet of said vacuum pump and having an inlet in fluid communication with said vacuum port and an outlet in fluid communication with said inlet of said vacuum pump, said waste canister system including a sealed and disposable waste container configured to substantially remove said abrasive material for at least temporary storage in said waste container.

14. An abrasive particle delivery and retrieval system comprising:
   a housing;
   a vacuum pump supported by said housing and having a vacuum inlet for creating a source of vacuum power;
   a vacuum control valve in fluid communication with said vacuum inlet for shunting air into said vacuum inlet to control the amount of vacuum transmitted by said vacuum pump;
   a vacuum port supported by said housing and in fluid communication with said vacuum inlet of said vacuum pump; and
   a supply container supported by said housing and having a supply port for supplying a flowing air carrying abrasive particles and an air inlet port
   a waste container interposed between said vacuum port and said vacuum inlet of said vacuum pump and having an inlet in fluid communication with said vacuum port and an outlet in fluid communication with said inlet of said vacuum pump, said waste container including at least a primary internal filter configured to substantially remove said abrasive material by causing all of said flowing air to pass through said primary filter.

15. The system as recited in claim 14 and further comprising a secondary filter interposed between said primary filter and said vacuum inlet of said vacuum pump and having a size of particulate filtration at least as small as a size of particulate filtration of said primary filter to further insure substantial removal of said abrasive material by causing all of said flowing air to also pass through said secondary filter and visibly seen from the exterior of said system.

16. The system as recited in claim 15 wherein said secondary filter is located outside said waste container and is independently supported by said housing.

17. The system as recited in claim 16 wherein said secondary filter is surrounded by a transparent filter cover accessible from outside of said housing to facilitate visual inspection and easy replacement of said secondary filter.

18. The system as recited in claim 14 and wherein said waste container further comprises:
   a collection canister having a lower container portion and a top plate having a central threaded bore and at least one collection hole spaced apart from said central threaded bore;
   a flexible flapper adjacent said at least one collection hole for flexing away from said at least one collection hole to enable material to flow into said lower container portion, said primary filter in a flow path between said at least one collection hole and said central threaded bore.

19. The system as recited in claim 18 and wherein said primary filter is formed as a hollow closed ended annular cylinder having side walls which are of an undulating shape for increased surface area to accommodate air flow.

20. An abrasive particle delivery and retrieval system comprising:
   a housing;
   a vacuum pump supported by said housing and having a vacuum inlet for creating a source of vacuum power;
   a vacuum control valve in fluid communication with said vacuum inlet for shunting air into said vacuum inlet to control the amount of vacuum transmitted by said vacuum pump;
   a vacuum port supported by said housing and in fluid communication with said vacuum inlet of said vacuum pump;
   a supply container supported by said housing and having a supply port for supplying a flowing air carrying abrasive particles and an air inlet port; and
   a supply container air control valve in fluid communication with said supply container to controllably limit air from the surrounding ambient atmosphere from entering said supply container.

21. An abrasive particle delivery and retrieval system comprising:
   a housing;
   a combination vacuum pump and pressurized air generation device supported by said housing and having a pressure outlet for transmitting a source of pressured air flow and having a vacuum inlet for creating a source of vacuum power;
   a mechanically connected motor to power said combination vacuum pump and pressurized air generation device;
   a vacuum control valve in fluid communication with said vacuum inlet for shunting air into said vacuum inlet to control the amount of vacuum transmitted by said vacuum pump;
   a vacuum port supported by said housing and in fluid communication with said vacuum inlet of said vacuum pump; and a supply container supported by said housing and having a supply port for supplying a flowing air carrying abrasive particles and an air inlet in fluid communication with said air inlet of said supply container.

22. The system as recited in claim 21 and further comprising a flow diversion valve in fluid communication with said pressure outlet for controllably reducing a pressure of said pressurized air by venting said pressurized air.

23. The system as recited in claim 22 wherein said flow diversion valve is a spring loaded manual actuation valve for quick control of said flow diversion valve.

24. The system as recited in claim 22 wherein said flow diversion valve is position selectable valve supported by said housing.

25. The system as recited in claim 24 wherein the displacement position of said position selectable valve is directly proportional to the flow of said pressurized air vented by said flow shunt valve.

26. The system as recited in claim 22 wherein said flow diversion valve is a first flow diversion valve, and further comprising a second flow diversion valve also in fluid communication with said pressure outlet for controllably providing a limit upon the amount of pressure of said pressure outlet despite operation of said first flow diversion valve to thereby provide an upper limit the pressure at said pressure outlet.

27. The system as recited in claim 21 and further comprising a relief valve in fluid communication with said air inlet of said supply container to enable a pre-determined amount of air to enter said supply container when pressure within said supply container drops below a pre-determined pressure.

28. The abrasion system as recited in claim 21 and further comprising a minimum vacuum threshold system further comprising:
 a vacuum switch in fluid communication with said vacuum port set to close when the pressure at said vacuum port is below a maximum threshold; and
 a diversion valve having an electrical actuator connected to said vacuum switch and located between said air inlet of said supply container and said pressurized air generation device for diverting air flow to controllably limit air entering said supply container when said pressure at said vacuum port is above said threshold, and to cease diverting air flow from entering said supply container when said pressure at said vacuum port is below said threshold, in order to prevent inadvertent transmission of abrasive material from said supply container through said supply port when an insufficient vacuum exists at said vacuum port.

29. The abrasion system as recited in claim 21 and further comprising a system purification filter located between said air inlet of said supply container and said pressurized air generation device for keeping unwanted particulate matter from entering said air inlet port of said supply container.

30. The abrasion system as recited in claim 21 and further comprising a purification heater located between said air inlet of said supply container and said pressurized air generation device for killing unwanted biological material before it enters said air inlet port of said supply container.

31. The abrasion system as recited in claim 21 and further comprising an ultraviolet purification system located between said air inlet of said supply container and said pressurized air generation device for exposing air from said pressurized air generation device to ultraviolet radiation to kill unwanted biological material in said exposed air before it enters said air inlet port of said supply container.

32. An abrasive particle delivery and retrieval system comprising:
 a housing;
 a vacuum pump supported by said housing and having a vacuum inlet for creating a source of vacuum power;
 a vacuum control valve in fluid communication with said vacuum inlet for shunting air into said vacuum inlet to control the amount of vacuum transmitted by said vacuum pump;
 a vacuum port supported by said housing and in fluid communication with said vacuum inlet of said vacuum pump; and
 a supply container supported by said housing and having a "U" shaped venturi tube having a first end opening to said supply container at a first vertical extent and extending downward to a "U" shaped section having an opening aperture for admitting abrasive particles and a second vertical extent from said "U" shaped section and having a second end opening for supplying flowing air carrying abrasive particles and terminating in a supply port supported by said housing, said supply container having an air inlet opening to a bottom of said supply container to fluidize any abrasive particulates located in said supply container.

33. An abrasive particle delivery and retrieval system comprising:
 a vacuum pump having a vacuum inlet for creating a source of vacuum power;
 a control valve in fluid communication with said vacuum inlet for shunting air into said vacuum inlet to control the amount of vacuum transmitted by said vacuum pump;
 a surface abrading tool having an outlet in fluid communication with said inlet of said vacuum pump, and an inlet;
 a supply of abrasive particles and air in flowing communication with said inlet of said surface abrading tool for supplying a flowing stream air carrying abrasive particles; and
 a sealed removable waste collection container interposed between said vacuum port and said vacuum inlet of said vacuum pump and having an inlet in fluid communication with said vacuum port and an outlet in fluid communication with said inlet of said vacuum pump, said waste collection space having at least a separator within said sealed removable waste collection container configured to substantially remove said abrasive material for at least temporary storage.

34. The system as recited in claim 33 wherein said sealed removable waste collection container includes means for admitting abrasive material when said vacuum pump is in operation and preventing a spillage of abrasive material from said waste collection container when said waste collection container is removed its position interposed between said vacuum port and said vacuum inlet of said vacuum pump.

35. The system as recited in claim 34 wherein said separator is a primary filter and wherein said waste collection space and said primary filter is configured to substantially remove said abrasive material by causing all of said flowing air to pass through said primary filter.

36. The system as recited in claim 35 and further comprising a secondary filter interposed between said primary filter and said vacuum inlet of said vacuum pump and having a size of particulate filtration at least as small as a size of particulate filtration of said primary filter to further insure substantial removal of said abrasive material by causing all of said flowing air to also pass through said secondary filter.

37. An abrasive particle delivery and retrieval system comprising:
   a vacuum pump having a vacuum inlet for creating a source of vacuum power;
   a control valve in fluid communication with said vacuum inlet for shunting air into said vacuum inlet to control the amount of vacuum transmitted by said vacuum pump;
   a surface abrading tool having an outlet in fluid communication with said inlet of said vacuum pump, and an inlet; and
   a supply of abrasive particles and air in flowing communication with said inlet of said surface abrading tool for supplying a flowing stream air carrying abrasive particles wherein said supply of abrasive particles has a air inlet and further comprising a supply air control valve having a first end in fluid communication with said supply of abrasive particles to controllably limit air entering said supply of abrasive particles from a second end open to said ambient surroundings, and a second end;
   a waste collection container interposed between said vacuum port and said vacuum inlet of said vacuum pump and having an inlet in fluid communication with said vacuum port and an outlet in fluid communication with said inlet of said vacuum pump, said waste collection space having at least a separator within said sealed removable waste collection container configured to substantially remove said abrasive material for at least temporary storage.

38. The system as recited in claim 37 and further comprising a pressurized air generation device having a pressure outlet for transmitting a source of pressured air flow in fluid communication with said air inlet of said supply of abrasive particles, said second end of said supply air control valve for controllably venting said source of pressured air flow.

39. The system as recited in claim 38 and further comprising a flow diversion valve in fluid communication with said pressure outlet of said pressurized air generation device for controllably reducing a pressure of said pressurized air by venting said pressurized air.

40. The system as recited in claim 39 wherein said flow diversion valve is a spring loaded manual actuation valve for quick control of said flow diversion valve.

41. The system as recited in claim 39 wherein said flow diversion valve is position selectable valve supported by said housing.

42. An abrasive particle delivery and retrieval system comprising:
   a vacuum pump having a vacuum inlet for creating a source of vacuum power;
   a control valve in fluid communication with said vacuum inlet for shunting air into said vacuum inlet to control the amount of vacuum transmitted by said vacuum pump;
   a surface abrading tool having an outlet in fluid communication with said inlet of said vacuum pump, and an inlet; and
   a supply of abrasive particles and air in flowing communication with said inlet of said surface abrading tool for supplying a flowing stream air carrying abrasive particles wherein said supply of abrasive particles has a air inlet and further comprising a supply air control valve having a first end in fluid communication with said supply of abrasive particles to controllably limit air entering said supply of abrasive particles from a second end open to said ambient surroundings, and a second end;
   a waste collection container interposed between said vacuum port and said vacuum inlet of said vacuum pump and having an inlet in fluid communication with said vacuum port and an outlet in fluid communication with said inlet of said vacuum pump, said waste collection space having at least a separator within said sealed removable waste collection container configured to substantially remove said abrasive material for at least temporary storage
   a pressurized air generation device having a pressure outlet for transmitting a source of pressured air flow in fluid communication with said air inlet of said supply of abrasive particles;
   a flow diversion valve in fluid communication with said pressure outlet of said pressurized air generation device for controllably reducing a pressure of said pressurized air by venting said pressurized air; and wherein said flow diversion valve is position selectable valve supported by said housing and wherein the displacement position of said position selectable valve is directly proportional to the flow of said pressurized air vented by said flow diversion valve.

43. An abrasive particle delivery and retrieval system comprising:
   a vacuum pump having a vacuum inlet for creating a source of vacuum power;
   a control valve in fluid communication with said vacuum inlet for shunting air into said vacuum inlet to control the amount of vacuum transmitted by said vacuum pump;
   a surface abrading tool having an outlet in fluid communication with said inlet of said vacuum pump, and an inlet;
   a supply of abrasive particles and air in flowing communication with said inlet of said surface abrading tool for supplying a flowing stream air carrying abrasive particles; and wherein said supply of abrasive particles has a air inlet and further comprising a supply air control valve having a first end in fluid communication with said supply of abrasive particles to controllably limit air entering said supply of abrasive particles, and a second end;
   a waste collection space interposed between said vacuum port and said vacuum inlet of said vacuum pump and having an inlet in fluid communication with said vacuum port and an outlet in fluid communication with said inlet of said vacuum pump, said waste collection space configured to substantially remove said abrasive material for at least temporary storage;
   a separator and wherein said waste collection space and said separator is configured to substantially remove said abrasive material by causing all of said flowing air to pass through said separator;
   a pressurized air generation device having a pressure outlet for transmitting a source of pressured air flow in fluid communication with one of said second end of said supply air control valve and said air inlet of said supply of abrasive particles;
   a flow diversion valve in fluid communication with said pressure outlet of said pressurized air generation device for controllably reducing a pressure of said pressurized air by venting said pressurized air; and wherein said flow diversion valve is a first flow diversion valve, and further comprising a second flow diversion valve also in fluid communication with said pressure outlet for controllably providing a limit upon the amount of pressure of said pressure outlet despite operation of said first flow diversion valve to thereby provide an upper limit the pressure at said pressure outlet.

* * * * *